US011059778B2

(12) United States Patent
Xie et al.

(10) Patent No.: US 11,059,778 B2
(45) Date of Patent: *Jul. 13, 2021

(54) CANNABINOID RECEPTOR CB2 LIGAND 4-(AMINOMETHYL)-N,N-DIALKYLANILINES

(71) Applicant: UNIVERSITY OF PITTSBURGH—OF THE COMMONWEALTH SYSTEM OF HIGHER EDUCATION, Pittsburgh, PA (US)

(72) Inventors: Xiang-Qun Xie, Sewickley, PA (US); Abdulrahman Almehizia, Pittsburgh, PA (US); Peng Yang, Pittsburgh, PA (US)

(73) Assignee: University of Pittsburgh - Of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/872,138

(22) Filed: May 11, 2020

(65) Prior Publication Data
US 2020/0270205 A1 Aug. 27, 2020

Related U.S. Application Data

(62) Division of application No. 15/580,539, filed as application No. PCT/US2016/038174 on Jun. 17, 2016, now Pat. No. 10,696,624.

(60) Provisional application No. 62/181,695, filed on Jun. 18, 2015.

(51) Int. Cl.
C07C 311/29 (2006.01)
C07D 405/12 (2006.01)
C07D 409/12 (2006.01)
C07D 333/34 (2006.01)
C07D 333/38 (2006.01)
C07C 311/13 (2006.01)
C07C 311/18 (2006.01)
C07D 401/12 (2006.01)
C07D 241/44 (2006.01)
A61P 19/10 (2006.01)
A61P 35/00 (2006.01)
C07D 213/42 (2006.01)
C07D 317/58 (2006.01)

(52) U.S. Cl.
CPC ............ C07C 311/29 (2013.01); A61P 19/10 (2018.01); A61P 35/00 (2018.01); C07C 311/13 (2013.01); C07C 311/18 (2013.01); C07D 213/42 (2013.01); C07D 241/44 (2013.01); C07D 317/58 (2013.01); C07D 333/34 (2013.01); C07D 333/38 (2013.01); C07D 401/12 (2013.01); C07D 405/12 (2013.01); C07D 409/12 (2013.01)

(58) Field of Classification Search
CPC ..................................................... C07C 311/29
USPC ......................................................... 344/355
See application file for complete search history.

(56) References Cited

U.S. PATENT DOCUMENTS 8,772,541 B2   7/2014  Xie
9,376,380 B2 * 6/2016  Xie ....................... C07C 311/48
9,656,981 B2   5/2017  Spigelman
2013/0172388 A1  7/2013  Xie et al.
2014/0296294 A1 10/2014  Xie et al.

OTHER PUBLICATIONS

Barbado Int. J. Cancer: 140, 674-685 (2017).*
Bab, Expert Rev. Endocrinol. Metab. 6(2), 135-138 (2011).*
Zhou et al., "Targeted Inhibition of the type 2 cannabinoid receptor is a novel approach to reduce renal fibrosis," Kidney Int., vol. 94, No. 4, pp. 756-772 (Oct. 2018).
Feng et al., "Targeting Cannabinoid Receptor-2 Pathway by Phenylacetylamide Suppresses the Proliferation of Human Myeloma Cells Through Mitotic Dysregulation and Cytoskeleton Disruption," Mol. Carcinog., vol. 54, No. 12, pp. 1796-1806 (Dec. 2015).
Cosman, "The Prevention and Treatment of Osteoporosis: A Review," Medscape General Medicine 7(2): 73 (2005).
Khajuria et al., "Drugs for the management of osteoporosis: a review," Rev. Bras. Reumatol. 51(4): 365-382 (2011).
McBane, "Osteoporosis: A review of current recommendations and emerging treatment options," published on Oct. 1, 2011 in Formulary Journal, pp. 432-446.
Mark Cooper, "Clinical Review—Osteoporosis," available at http://www.gponline.com/clinical-review-osteoporosis/rheumatology/osteoporosis-and-bone-disorders/article/1119708 (published on Mar. 7, 2012), 8 pages.
Feng, et al., "Modeling, Molecular Dynamics Simulation, and Mutation Validation for Structure of Cannabinoid Receptor 2 Based on Known Crystal Structures of GPCRs," Journ. of Chemical Information and Modeling, vol. 54, pp. 2483-2499 (Aug. 2014).
Yang et al., "Lead Discovery, Chemistry Optimization, and Biological Evaluation Studies of Novel Biamide Derivatives as CB(2) Receptor Inverse Agonists and Osteoclast Inhibitors," J Med Chem., 55(22):9973-9987 (2012).
Zhang et al., "Mutagenesis and computer modeling studies of a GPCR conserved residue W5.43(194) in ligand recognition and signal transduction for CB2 receptor," Int. Immunopharmacol., 11(9):1303-1310 (2011).
Gertsch, J., et al., Beta-caryophyllene is a dietary cannabinoid. Proc Natl Acad Sci, vol. 105 (26), 9099-9104 (2008).
Feng, R., et al., "SDX-308, a nonsteroidal anti-inflammatory agent, inhibits NF-kappaB activity, resulting in strong inhibition of osteoclast formation/activity and multiple myeloma cell growth," Blood, vol. 109 (5), 2130-2138 (2007).

(Continued)

Primary Examiner — Nizal S Chandrakumar
(74) Attorney, Agent, or Firm — Foley & Lardner LLP

(57) ABSTRACT

Disclosed herein are novel cannabionid receptor-2 (CB2) agonists and inverse agonists represented by Formula (I), and method of modulating the activity of CB2 by contacting the CB-2 receptor with a compound of Formula (I). Also, disclosed are methods for treating multiple myeloma or osteoporosis in a mammal in need thereof by modulating the activity of a cannabinoid receptor-2 (CB2).

21 Claims, 7 Drawing Sheets

(56) References Cited

OTHER PUBLICATIONS

Yu, M., et al., "Curcumol suppresses RANKL-induced osteoclast formation by attenuating the JNK signaling pathway," *Biochem Biophys Res Commun.*, vol. 447 (2), 364-70 (2014).
Feng, R., et al., "KD5170, a novel mercaptoketone-based histone deacetylase inhibitor, exerts antimyeloma effects by DNA damage and mitochondrial signaling," *Mol Cancer Ther.*, vol. 7 (6), 1494-1505 (2008).
Ofek et al., Peripheral cannabinoid receptor, CB2, regulates bone mass. *Proc Natl Acad Sci.*, vol. 103 (3), pp. 696-701 (2006).
Bab et al., "Cannabinoid receptors and the regulation of bone mass," *Br. J. Pharmacol*, vol. 153 (2), 182-188 (2008).
Bab et al., "Cannabinoids and the skeleton: from marijuana to reversal of bone loss," *Ann Med.*, vol. 41 (8), pp. 560-567 (2009).
Idris et al., Regulation of bone mass, osteoclast function, and ovariectomy-induced bone loss by the type 2 cannabinoid receptor. *Endocrinology*, vol. 149 (11), 5619-5626 (2008).
van Meerloo, J, et al., Cell sensitivity assays: the MTT assay. *Methods Mol Biol*, vol. 731, pp. 237-245 (2011).
Bodor, N., "Novel Approaches in Prodrug Design," *Drugs of the Future*, vol. 6, pp. 165-182 (1981).
Bundgaard, H., "Design of Prodrugs: Bioreversible-Derivatives for Various Functional Groups and Chemical Entities," in Design of Prodrugs, Elsevier (1985), 1 page Abstract.
Notari, "Theory and Practice of Prodrug Kinetics," *Methods in Enzymology*, vol. 112, pp. 309-323 (1985).
International Preliminary Report on Patentability issued in International Patent Application No. PCT/US2016/038174, completed Dec. 28, 2017.
International Search Report and Written Opinion issued in related International Patent Application No. PCT/US2016/038174, dated Nov. 22, 2016.
Batra, Biochemical Pharmacology (1988), 37(13), pp. 2595-2602.
Ouyang, ACS Medicinal Chemistry Letters (2013), 4(4), pp. 387-392.
Yang, Journal of Medicinal Chemistry (2013), 56(5), pp. 2045-2058.

* cited by examiner

CANNABINOID RECEPTOR CB2 LIGAND 4-(AMINOMETHYL)-N, N-DIALKYLANILINES

CROSS-REFERENCE TO RELATED APPLICATIONS

This application is a divisional of U.S. patent application Ser. No. 15/580,539, filed Dec. 7, 2017, which is the U.S. National Stage of International Patent Application No. PCT/US2016/038174, filed Jun. 17, 2016, which claims priority to U.S. Provisional Patent Application No. 62/181,695, filed Jun. 18, 2015. The contents of these applications are incorporated herein by reference in their entirety.

This invention was made with government support under NIH grant # DA025612 awarded by the NIH. The government has certain rights in the invention.

BACKGROUND

The field of cannabinoid research has gained attention in recent years, particularly in view of the legal use of medical marijuana now approved in several states. However, medical marijuana or cannabinoid (CB) has reached certain limitation. Cannabinoid (CB) drug research also faces a great challenge because the CB1 antagonist drug Rimonabant was recently withdrawn from the European market due to the complications of suicide and depression trends associated with the inhibition of CB receptor subtype CB1. Hence, there is a need to develop CB2-selective drugs lacking psychotropic side effects caused by interaction with CB1.

Multiple myeloma: Multiple myeloma (MM) is an uncontrolled differentiation of plasma B cells and the accumulation in the bone marrow. MM accounts for 10% of blood cancers and more than 22,000 new cases are diagnosed yearly in the United States. MM is associated with aggressive clinical manifestations including hematological and metabolic diseases. In addition, bone complications are common in more than 60% of cases such as osteoporosis, bone lesions and fractures. Complicated molecular signaling pathogenesis pathways are involved in the MM disease which accounts for the difficult disease control. MM remains an incurable disease despite the recent discovery of novel proteasome inhibitor (Bortezomib). Further, about 30% of patients with MM never respond to Bortezomib treatment.

Osteoporosis: Nearly 45 million Americans are facing a major bone health threat, among which 10 million individuals already have osteoporosis (OP), a metabolic bone disease, and the remaining 35 million are at high risk for OP. Current medications used to treat osteoporosis often have severe adverse effects limiting their usage. For example, bisphosphonate drugs have a severe side effect called bisphosphonate-associated osteonecrosis of the jaw via undefined mechanism(s). Also, parathyroid hormone (PTH) is a costly drug and has an FDA black-box warning due to its association with an increased risk of osteosarcoma. Most importantly, osteoporosis is involved in complicated pathways that are still not fully understood.

Novel molecular targets and related chemical probes are needed to overcome the chemoresistance of MM and facilitate novel MM drug discovery. In addition, there is an urgent demand for conducting innovative research to study the underlying mechanisms of OP as well as searching for novel drugs with specific targets to treat OP. The present invention satisfies these needs.

SUMMARY OF THE INVENTION

One embodiment of the invention relates to compounds represented by Formula (I):

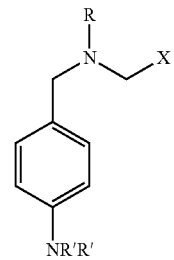

wherein (i) R is A-B-Y; (ii) A is —$SO_2$— or —C(O)—; (iii) B is a bond or —CHCH—; (iv) X is selected from the group consisting of substituted phenyl, substituted or unsubstituted pyridine; substituted or unsubstituted $C_{3-5}$ alkyl, wherein the substituted phenyl, pyridine and alkyl is substituted with two or three moieties selected from $C_{1-4}$ alkyl, $C_{1-4}$ alkoxy, —C(O)H, $C_{1-4}$ perfluroalkyl, and $C_{1-4}$ perfluroalkoxy, or the substituted phenyl or pyridine is substituted with —O—$(CH_2)_{1-2}$—O— where the O molecules are covalently bound to adjacent carbon atoms on the substituted phenyl or pyridine; (v) Y is a ringed moiety selected from phenyl, naphthyl, and thiophenyl, wherein one or two of the ring carbons is optionally replaced with N, and wherein the ringed moiety is optionally substituted with one to three $C_{1-4}$ alkyl, $C_{1-4}$ alkoxy, —C(O)H, $C_{1-4}$ perfluroalkyl, $C_{1-4}$ perfluroalkoxy or phenyl; and (vi) R' is, in each instance a $C_{1-6}$ alkyl, or a pharmaceutically acceptable salt thereof.

In some embodiments, in Formula (I), A is —$SO_2$— or A is —C(O)—.

In some embodiments, in Formula (I), B is a bond. In other embodiments, B is —CHCH—, which may be trans, cis, or a mixture thereof.

In some embodiments, in Formula (I), X is phenyl substituted with three $C_{1-4}$ alkoxy, preferably methoxy or ethoxy. Other embodiments include wherein X is phenyl substituted with three methoxy or ethoxy, for example, at the meta and para positions. In other embodiments, X is phenyl substituted with —O—$(CH_2)_{1-2}$—O—, for example at a meta and the para positions, or at an ortho and a meta position. In other embodiments, X is unsubstituted pyridine, or X is pyridine substituted with —O—$(CH_2)_{1-2}$—O—. Each carbon position of the pyridine may be the point of attachment for the pyridine ring, however, the preferred position is the 3-position, i.e.,

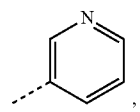

wherein the dashed line represents the covalent bond to the adjacent alkylene in the Formula I. Other embodiments include wherein X is an unsubstituted $C_{3-5}$ alkyl, for example, n-propyl, n-butyl, n-pentyl. Preferably, X is selected from

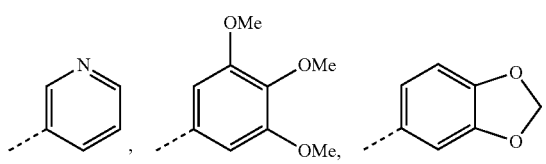

and n-pentyl.

In some embodiments, in Formula (I), Y is phenyl, or is phenyl, and is substituted only at the para position, or only at the ortho position.

In some embodiments, in Formula (I), R is selected from the R groups in Tables 1-4. In some embodiments, in Formula (I), Y is selected from the Y groups in Tables 1-4. It is understood that the R groups in Tables 1-4 can each be separated into "A-B-Y," as explained for Formula I.

In some embodiments, the compounds of Formula I do not include the specific embodiments described in US 2014-0296294 for "Novel Cannabinoid Receptor 2 (Cb2) Inverse Agonists And Therapeutic Potential For Multiple Myeloma And Osteoporosis Bone Diseases."

Another embodiment of the invention relates to a pharmaceutical composition comprising a compound selected from any of the embodiments of Formula I, or a pharmaceutically acceptable salt thereof, and at least one pharmaceutically acceptable excipient.

Another embodiment of the invention relates to a method for treating multiple myeloma in a mammal in need thereof by modulating the activity of a cannabinoid receptor-2 (CB2), comprising administering to the mammal a therapeutically effective amount of a compound selected from any of the embodiments of Formula I, or a pharmaceutically acceptable salt thereof.

Yet another embodiment of the invention relates to a method for treating osteoporosis in a mammal in need thereof by modulating the activity of a cannabinoid receptor-2 (CB2), comprising administering to the mammal a therapeutically effective amount of a compound selected from any of the embodiments of Formula I, or a pharmaceutically acceptable salt thereof.

Another embodiment of the invention relates to a method for modulating the activity of a cannabinoid receptor-2 (CB2) in a mammal in need thereof, comprising contacting the CB-2 receptor with a compound selected from any of the embodiments of Formula I, or a pharmaceutically acceptable salt thereof.

The foregoing general description and following brief description of the drawings and detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF FIGURES

FIG. 5A: Compounds 15 and 18 inhibited the RANKL-induced osteoclast differentiation in a dose-dependent manner. Compound 11 had low effect in inducing the osteoclast formation at higher doses. FIG. 5B: BM cells were seeded at a density of 2×105 cells/well in 96-well plates and treated with or without RANKL (100 ng/mL) and M-CSF (30 ng/mL). CB2 compounds were added at the indicated concentrations for 10 days and stained for TRAP expression. Data is the mean of three experiments carried out in triplicates. (B) Microscopic photographs of cells for compound 15 (magnification 100×).

FIG. 5A: Cytotoxicity effects of compound 15. FIG. 5B: Cytotoxicity effects of compound 18. Osteoclast precursor RAW264.7 cells (1.5×103 cells/well) were seeded on 96-well plates. Cells were incubated with the indicated doses of compounds 15 and 18 for 48 hours. The percentage of cell survival was determined by the MTT assay. Data is the mean±SD of three experiments carried out in duplicate.

DETAILED DESCRIPTION

1. Compounds of the Invention

Figure 1:
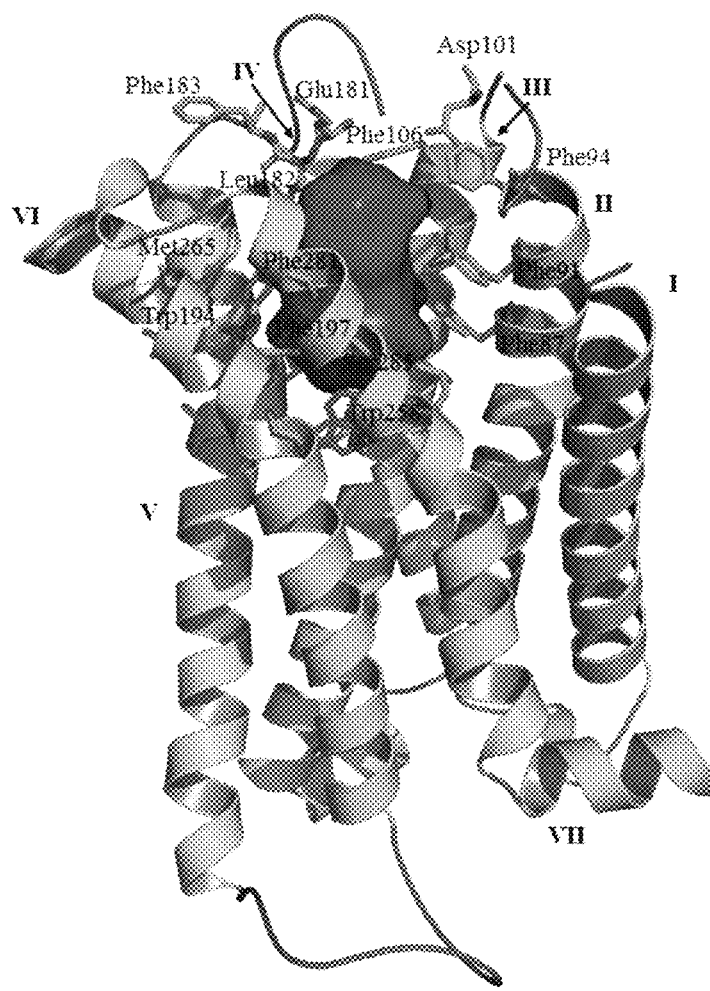
FIG. 1 relates to the CB2 homology model and the potential binding pocket. The potential binding pocket is formed by helices III, V, VI, and VII. Important amino acids in the pocket are: Phe872.57, Phe912.61, Phe942.64, Asp101 (ECL1), Phe1063.25, Lys1093.28, Ile1103.29, Val1133.32, Phe1173.36, Glu181 (ECL2), Leu182 (ECL2), Phe183 (ECL2), Trp1945.43, Phe1975.46, Trp2586.48, Val2616.51, Met2656.55, Phe2817.35, and Ser2857.39.
Figure 2:
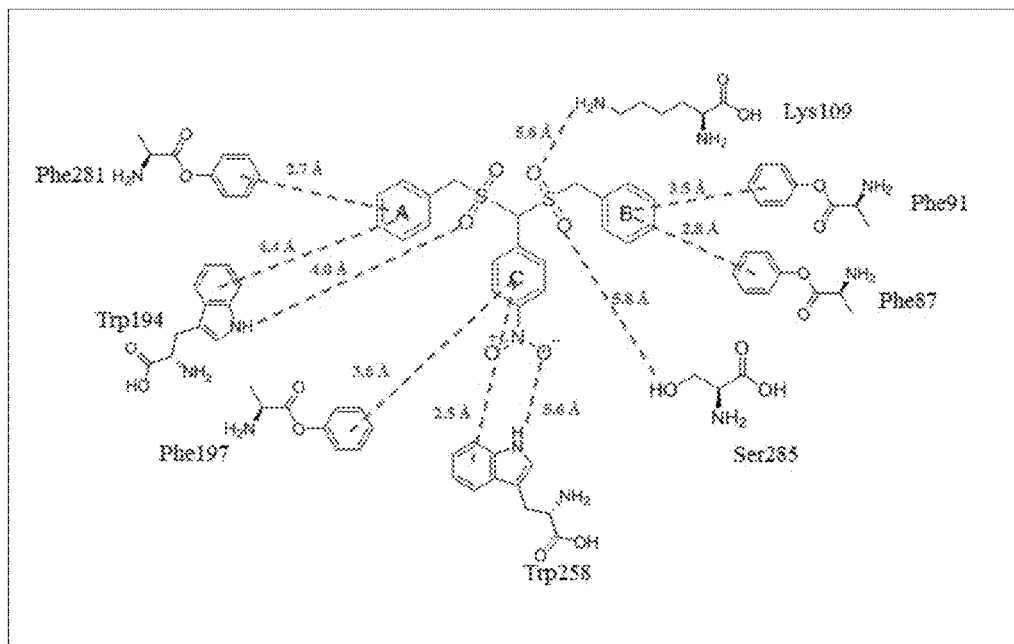
FIG. 2 relates to molecular docking interaction of compound 1 with the important amino acids in the CB2 binding pocket. Hydrophobic interactions were observed between Phe281 and Trp194 with ring A. Hydrogen bonding interaction was observed between Trp194 and the sulfonyl group of ring A. Similarly, hydrophobic interactions were observed between rings B and C with Phe197, Phe91, and Phe87.
Figure 3:
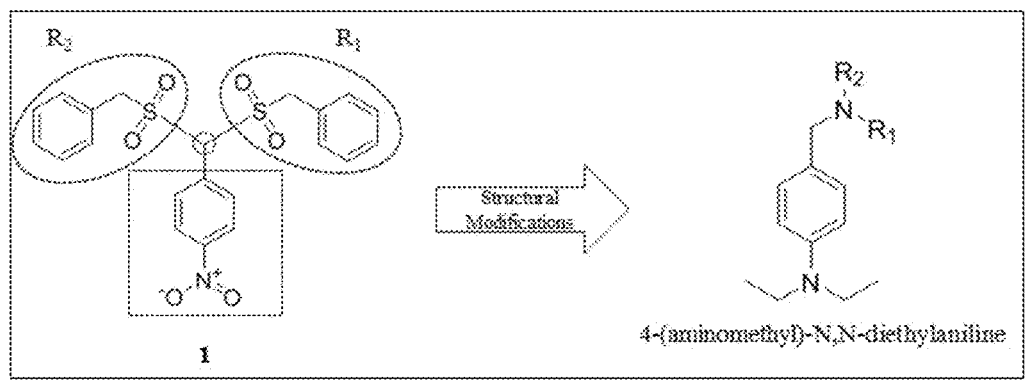
FIG. 3 relates to lead optimization strategies. The lead compound 1 optimization strategies were: a) replace the para-nitro group with diethylamine moiety; b) change the central chiral carbon atom to a nitrogen center; and c) introduce different fragments at positions R1 and R2.

Compounds of the present disclosure include novel compounds represented by Formula (I):

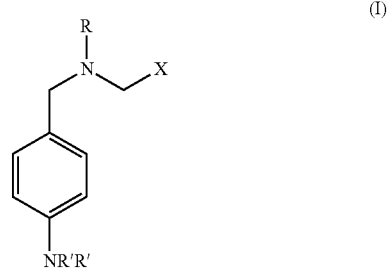

wherein:

R is A-B-Y;

A is —SO$_2$— or —C(O)—;

B is a bond or —CHCH—;

X is selected from the group consisting of substituted phenyl, substituted or unsubstituted pyridine; and substituted or unsubstituted C$_{3-5}$ alkyl, wherein the substituted phenyl, pyridine and alkyl is substituted with two or three moieties selected from C$_{1-4}$ alkyl, C$_{1-4}$ alkoxy, —C(O)H, C$_{1-4}$ perfluroalkyl, and C$_{1-4}$ perfluroalkoxy, or the substituted phenyl or pyridine is substituted with —O—(CH$_2$)$_{1-2}$—O— where the O molecules are covalently bound to adjacent carbon atoms on the substituted phenyl or pyridine;

Y is a ringed moiety selected from phenyl, naphthyl, and thiophenyl, wherein one or two of the ring carbons is optionally replaced with N, and wherein the ringed moiety is optionally substituted with one to three C$_{1-4}$ alkyl, C$_{1-4}$ alkoxy, —C(O)H, C$_{1-4}$ perfluroalkyl, C$_{1-4}$ perfluroalkoxy or phenyl; and R' is, in each instance a C$_{1-6}$ alkyl, or a pharmaceutically acceptable salt thereof.

In some embodiments, in Formula (I), A is —SO$_2$— or A is —C(O)—.

In some embodiments, in Formula (I), B is a bond. In other embodiments, B is —CHCH—, which may be trans, cis, or a mixture thereof.

In some embodiments, in Formula (I), X is phenyl substituted with three C$_{1-4}$ alkoxy, preferably methoxy or ethoxy. Other embodiments include wherein X is phenyl substituted with three methoxy or ethoxy, for example, at the meta and para positions. In other embodiments, X is phenyl substituted with —O—(CH$_2$)$_{1-2}$—O—, for example at a meta and the para positions, or at an ortho and a meta position. In other embodiments, X is unsubstituted pyridine, or X is pyridine substituted with —O—(CH$_2$)$_{1-2}$—O. Each carbon position of the pyridine may be the point of attachment for the pyridine ring, however, the preferred position is the 3-position, i.e.,

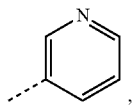

wherein the dashed line represents the covalent bond to the adjacent alkylene in the Formula I. Other embodiments include wherein X is an unsubstituted C$_{3-5}$ alkyl, for example, n-propyl, n-butyl, n-pentyl. Preferably, X is selected from

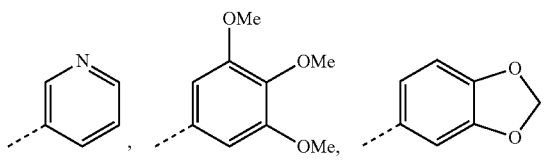

and n-pentyl.

In some embodiments, in Formula (I), Y is phenyl, or is phenyl, and is substituted only at the para position, or only at the ortho position.

In some embodiments, in Formula (I), R is selected from the R groups in Tables 1-4. In some embodiments, in Formula (I), Y is selected from the Y groups in Tables 1-4. It is understood that the R groups in Tables 1-4 can each be separated into "A-B-Y," as explained for Formula I.

In some embodiments, the compounds of Formula I do not include the specific embodiments, U.S. patent Ser. No. 14/305,941, which is hereby incorporated by reference in its entirety.

2. Methods of Treatment

In one embodiment, encompassed is a method for treating multiple myeloma in a subject by modulating the activity of a cannabinoid receptor-2 (CB2), comprising administering to the subject a pharmaceutical composition comprising a therapeutically effective amount of a compound of Formula I. Also encompassed is a method for treating osteoporosis in a subject by modulating the activity of a cannabinoid receptor-2 (CB2), comprising administering to the subject a pharmaceutical composition comprising a therapeutically effective amount of a compound of Formula I. In another aspect, encompassed is a method for modulating the activity of a cannabinoid receptor-2 (CB2) in a subject, comprising contacting a cannabinoid receptor-2 (CB2) receptor with a compound of Formula I.

The compositions may be administered via any pharmaceutically acceptable method. For example, the compositions can be administered topically, orally, bucally, inhalation, pulmonary, sublingually, intranasally, parenterally, subcutaneously, intradermally, intravenously, intraperitoneally, intramuscularly, epidurally, parenterally, intranasally, and/or intracranially. Parenteral or systemic administration includes, but is not limited to, subcutaneous, intravenous, intraperitoneally, intramuscular, intra-articular, intrasynovial, intrasternal, intrathecal, intralesional, intracranial injections, or infusion techniques.

Suitable oral compositions in accordance with the invention include without limitation tablets, troches, lozenges, aqueous or oily suspensions, dispersible powders or granules, emulsion, hard or soft capsules, syrups or elixirs. The dosage form may be a single unit dosage form that includes any of the compounds of Formula I, or a pharmaceutically salt thereof. Such dosage forms may include one or more pharmaceutically acceptable carriers.

Compounds of Formula I (including all sub-formulae), or pharmaceutically acceptable salts or solvates thereof, or a composition comprising such a compound or a pharmaceutically acceptable salt or solvate thereof, can be administered to a patient or subject in need of treatment either individually, or in combination with other therapeutic agents, such as therapeutic agents that have similar biological activities. For example, Formula I compounds and compositions can be administered as a single dose or as multiple daily doses by a practicing medical practitioner. When combination therapy is used, however, the compound and the other therapeutic agent can be administered separately at different time intervals, or simultaneously.

In in some embodiments, the subject is a mammal, preferably a human.

A. Osteoporosis

Medications for treating osteoporosis include two types: anti-resorptive medications which reduce rates of bone remodeling; and anabolic medications which stimulate new bone formation, repair architectural defects and improve bone density. Anti-resorptive medications include, for example, estrogens, selective estrogen receptor modulators (SERMs) (e.g., raloxifene and tamoxifen), bisphosphonates (e.g., alendronate, risedronate, and ibandronate) and calcitonins. Teriparatide, which is a parathyroid hormone, is the only anabolic medicine currently approved in the U.S. for treating osteoporosis. "The Prevention and Treatment of Osteoporosis: A Review," *Medscape General Medicine* 7(2): 73 (2005).

There are disadvantages or undesired side effects associated with the currently available osteoporosis medications, including efficacy and long-term safety concerns. More specifically, estrogen therapy may cause some non-skeletal adverse effects such as increased risk for vascular events and breast cancer. SERMs such as raloxifene and tamoxifen are reported to increase the risk of venous thromboembolic events, increase the occurrence of hot flashes and cause leg cramps. Bisphosphonates are associated with low anti-fracture efficacy (reported to be only about 50%) and low bioavailability. Moreover, oral administration of bisphosphonates causes upper gastrointestinal (GI) intolerance. Clinically, bisphosphonates prescription is avoided in pre-menopausal women and patients with significant renal impairment or existing upper GI pathology. Some rare but severe side effects associated with bisphosphonates include osteonecrosis of the jaw (ONJ) and atypical femur fracture. Accordingly, the duration of bisphosphonates treatment will be an issue for treating the chronic condition of osteoporosis. Calcitonin is used to treat or prevent vertebral fractures and available in a nasal spray formulation, which causes nasal irritation and occasional epistaxis in some patients. However, calcitonin has not shown consistent, satisfactory effects on non-vertebral or hip fractures. See Khajuria et al., "Drugs for the management of osteoporosis: a review," *Rev. Bras. Reumatol.* 51(4): 365-382 (2011); Mark Cooper, "Clinical Review—Osteoporosis," available at http://www.gponline.com/clinical-review-osteoporosis/rheumatology/osteoporosis-and-bone-disorders/article/1119708 (published on Mar. 7, 2012); and McBane, "Osteoporosis: A review of current recommendations and emerging treatment options," published on Oct. 1, 2011 in Formulary Journal, available at http://formularyjournal.modernmedicine.com/print/136829. Therefore, calcitonin is not considered a satisfactory treatment option for patients having increased risk of osteoporosis due to pelvic radiotherapy, who are prone to hip fractures.

Figure 5A:
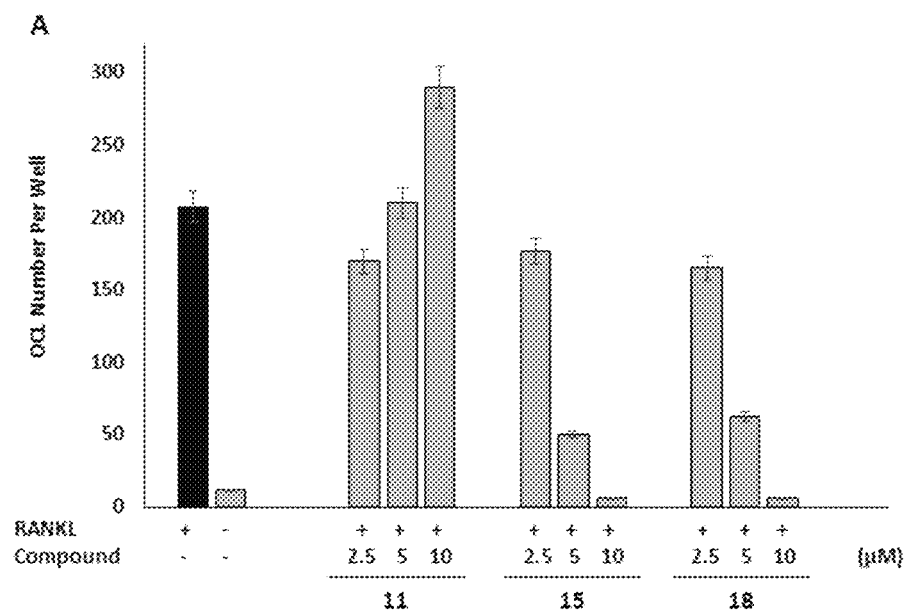
FIGS. 5A and 5B relate to cAMP Assay Results. Anti-osteoclastogenesis activity of the synthesized CB2 ligands.
Figure 5B:
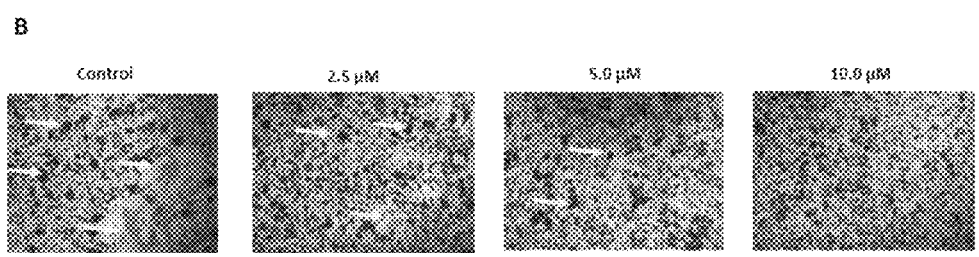
Figures 6A, 6B:
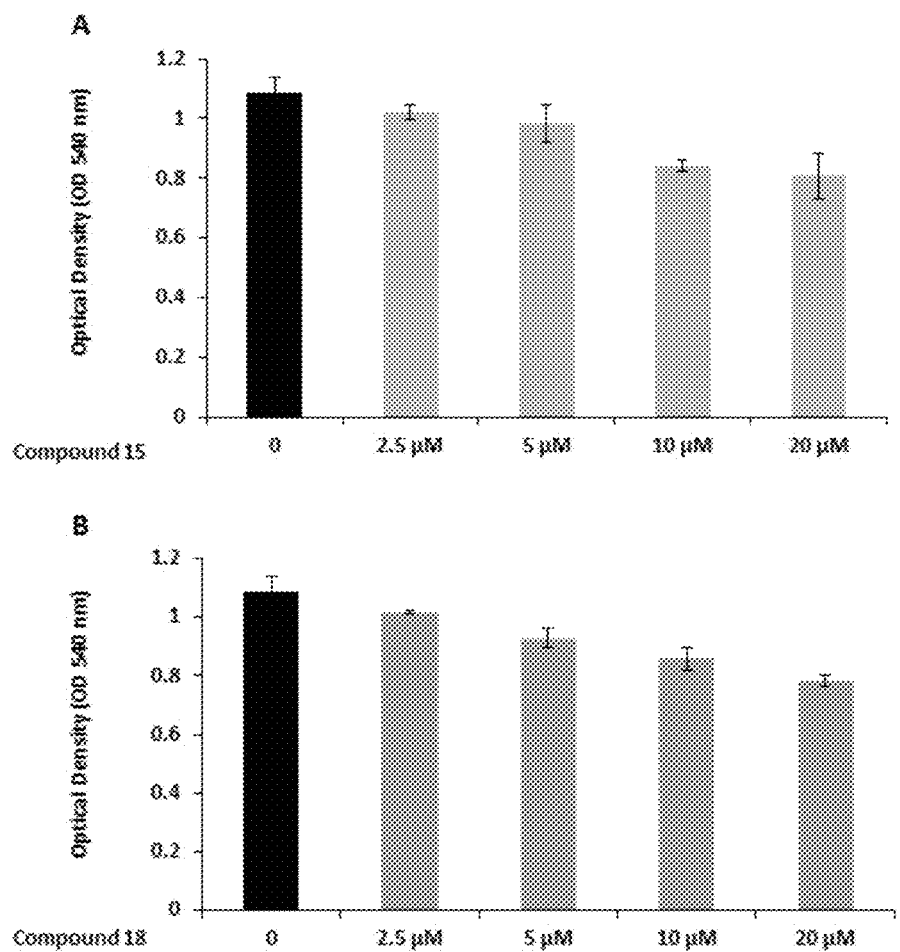
FIGS. 6A and 6B relate to cAMP Assay Results. Cytotoxicity effects of the synthesized CB2 ligands.
Figure 7:
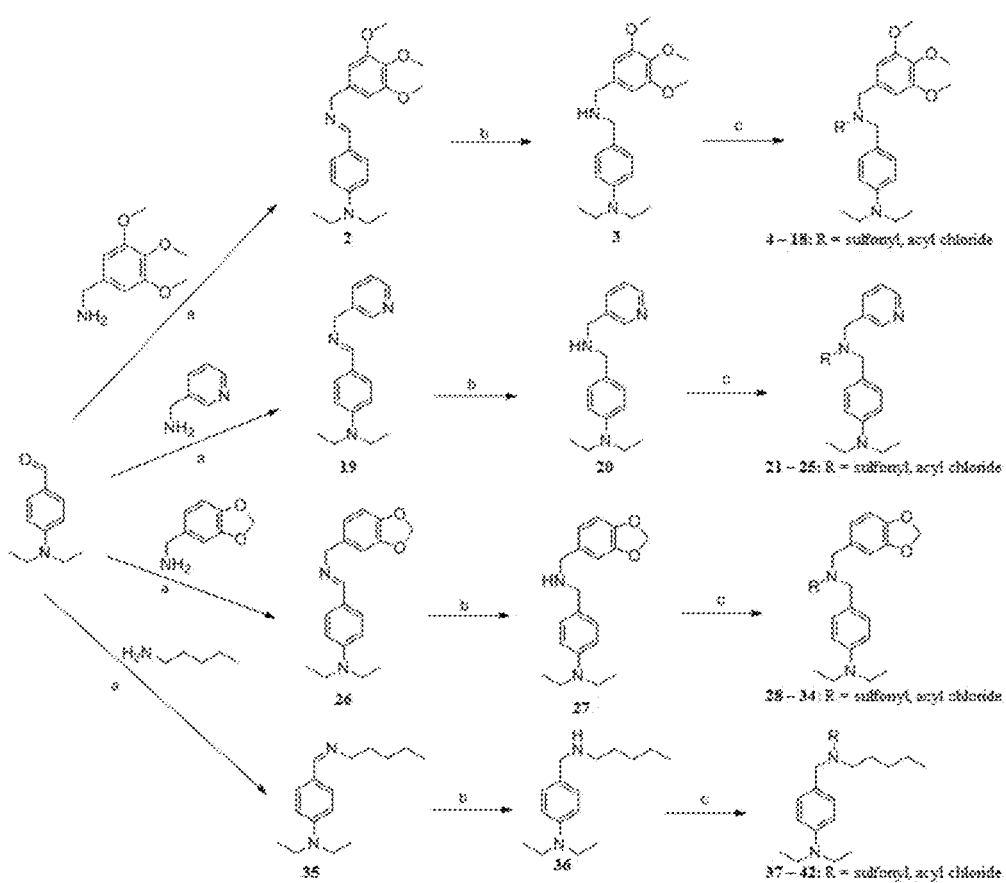
FIG. 7 relates to synthesis routes for 4-(aminomethyl)-N, N-diethylaniline derivatives. Reagents and conditions: (a) methanol, refluxed, 10 hours; (b) NaBH₄, methanol, rt, 12 hours; (c) sulfonyl chloride or acyl chloride, anhydrous dichloromethane, triethylamine, rt, 12 hours; (d) R—Br, acetone, refluxed, 10 hours.

As described in the examples below, cannabinoids have been known to modulate and maintain bone remodeling and balance. In addition, CB2 receptors have been shown to be involved in osteoporosis, suggesting the CB2 receptors as promising targets for osteoporosis. Three compounds described in the Examples below (15, 18, and 11) were selected to evaluate their activity against the receptor-activator of nuclear factor kappa-B ligand (RANKL)-induced osteoclast differentiation on 4- to 6-week old C57BL/6 mouse bone marrow cells. As shown in FIG. 5, compounds 15 and 18 induced a concentration-dependent inhibition of osteoclast formation showing a strong inhibition at 10 µM (inhibition rates>95%). These results are consistent with their CB2 binding affinity. However, compound 11 showed an induction of osteoclast formation at higher doses (10 µM). This data suggests that CB2 inverse agonists are more promising than CB2 agonists for the inhibition of osteoclast formation and ultimately for osteoporosis treatment.

A cytotoxicity assay was carried out to exclude that the high osteoclast formation inhibition effects were not due to the toxicity of the newly discovered compounds. The cytotoxic effects were measured by utilizing the MTT cell-viability assay. As shown in FIG. 5, cell viability was not significantly altered by the tested compound as compared to the control group. Both compounds had minimal effects at doses of 2.5, 5.0, and 10 µM with low effects at higher doses (20 µM). These results showed that the good anti-osteoclast activity of the newly discovered compounds was not due to their cytotoxicity, which means favorable therapeutic indices of the new CB2 ligands.

Thus, in one embodiment, the present invention is directed to a method of preventing and/or treating osteopenia, osteoporosis, or bone loss in a subject, wherein the method comprises administering a pharmaceutical composition according to the invention to a subject in need. The subject can be a mammal such as human. In one embodiment, the mammal to be treated has osteopenia, osteoporosis, or bone loss, or is at risk of osteopenia, osteoporosis or bone loss.

In some embodiments, the subject is a post-menopausal woman who suffers from bone loss or post-menopausal osteoporosis. In other embodiments, the subject is a cancer patient who received chemotherapy or radiation therapy, particularly, pelvic radiotherapy that can cause damage to the bones. In yet other embodiments, the subject is at increased risk of bone loss or osteoporosis due to aging, menopause, other medications, therapies, or any combination thereof.

In another embodiment, the invention encompasses methods comprising: (i) performing a bone scan or any other means to measure bone density to assess the bone density of the subject to determine whether the subject suffers from osteopenia, osteoporosis, or bone loss, or whether the subject has declining bone density suspected to lead to osteopenia, osteoporosis or bone loss; and (ii) administering an effective therapeutic amount of a composition according to the invention to a subject in need. A "subject in need" includes subjects who suffer from osteopenia, osteoporosis, or bone loss, or subjects that have declining bone density suspected to lead to osteopenia, osteoporosis or bone loss.

In other embodiments, a composition according to the invention is co-administered before, during, or after administration of a drug useful in treating and/or preventing osteoporosis. The composition according to the invention can be administered at any suitable time point before, during, or after the administration of an osteoporosis drug, or the composition according to the invention can be combined with the osteoporosis drug for administration.

The composition according to the invention, when co-administered with an osteoporosis drug, can be administered before, during, or after administration of the osteoporosis drug. In one embodiment, the composition according to the invention can be administered up to about 72 hours before administration of the osteoporosis drug, up to about 10 days after administration of the osteoporosis drug, or any combination thereof. In other examples, the composition according to the invention and the osteoporosis drug can be administered in a time frame selected from the group consisting of: (a) within about 36 hours of each other; (b) within about 12 hours of each other; or (c) within about 6 hours of each other. Other time periods for administering the IL-12 composition include but are not limited to at about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 30, about 36, about 42, about 48, about 54, about 60, about 66, or about 72 hours before the administration of the osteoporosis drug. Other time periods for administration of the IL-12 composition include but are not limited to administration at about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 30, about 36, about 42, about 48, about 54, about 60, about 66 hours, about 3 days, about 4 days, about 5 days, about 6 days, about 7 days, about 8 days, about 9 days, or about 10 days after administration of the osteoporosis drug, or any combination of the foregoing time periods.

In some embodiments of the invention, the composition according to the invention can be administered weekly, bi-weekly, monthly, bi-monthly, or any other suitable interval period between dosing, and which can extend for any desirable period of time, including for up to about 1, about 2, about 3, about 4, about 5, about 6, about 7, about 8, about 9 or about 10 years or more. In some embodiments, the composition according to the invention is administered once every month for up to 6 months.

In some embodiments of the invention, a single dose of a composition according to the invention can be administered each month for a treatment period of 3 months, 4 months, 5 months or 6 months is sufficient to prevent or treat osteopenia, osteoporosis, or bone loss, or to alleviate the condition of osteopenia, osteoporosis, or bone loss whether alone or in combination with another anti-osteoporosis drug. In other embodiments, the composition according to the invention can be additionally administered for another period of 3 months, 4 months, 5 months, 6 months, 7 months, 8 months, 9 months, 10 months, 11 months, or 12 months. In addition, the treatment cycle of the composition according to the invention can be repeated one or more times following the initial administration, and each cycle independently can be a period of 3 months, 4 months, 5 months, 6 months, 7 months, 8 months, 9 months, 10 months, 11 months, or 12 months.

Optionally, a bone scan is performed after the first 6 months of administration of a composition according to the invention to assess the bone density, and if necessary, the composition is administered once every month for additional 6 months, 7 months, 8 months, 9 months, 10 months, 11 months, or 12 months, or any other time period or dosing schedule described herein.

B. Multiple Myeloma

The data described herein also teaches usefulness of the compositions according to the invention in treating multiple myeloma. Multiple myeloma, also known as plasma cell myeloma, myelomatosis, or Kahler's disease, is a cancer of plasma cells, a type of white blood cell normally responsible for producing antibodies. In multiple myeloma, collections of abnormal plasma cells accumulate in the bone marrow, where they interfere with the production of normal blood cells.

Multiple myeloma is considered to be incurable but treatable. Remissions may be induced with steroids, chemotherapy, proteasome inhibitors, immunomodulatory drugs such as thalidomide or lenalidomide, and stem cell transplants. Radiation therapy is sometimes used to reduce pain from bone lesions.

Treatment for multiple myeloma is focused on therapies that decrease the clonal plasma cell population and consequently decrease the signs and symptoms of disease. In addition to direct treatment of the plasma cell proliferation, bisphosphonates (e.g., pamidronate or zoledronic acid) are routinely administered to prevent fractures; they have also been observed to have direct anti-tumor effect even in patients without known skeletal disease. If needed, red blood cell transfusions or erythropoietin can be used for management of anemia. Bortezomib has the first therapeutic proteasome inhibitor approved by the U.S. FDA for treating relapsed multiple myeloma.

Initial treatment of multiple myeloma depends on the patient's age and comorbidities. In recent years, high-dose chemotherapy with autologous hematopoietic stem-cell transplantation has become the preferred treatment for patients under the age of 65. Prior to stem-cell transplantation, these patients receive an initial course of induction chemotherapy. The most common induction regimens used today are lenalidomide-dexamethasone, bortezomib based regimens, and lenalidomide-dexamethasone. Autologous stem cell transplantation (ASCT), the transplantation of a patient's own stem cells after chemotherapy, is the most common type of stem cell transplantation for multiple myeloma. It is not curative, but does prolong overall survival and complete remission. Allogeneic stem cell transplantation, the transplantation of a healthy person's stem cells into the affected patient, has the potential for a cure, but is used in a very small percentage of patients (and in the relapsed setting, not as part of initial treatment). Furthermore, there is a 5-10% treatment-associated mortality rate.

Thus, in one embodiment, the present invention is directed to a method of treating multiple myeloma in a subject, wherein the method comprises administering a pharmaceutical composition according to the invention to a subject in need. The subject can be a mammal such as human.

In other embodiments, a composition according to the invention is co-administered before, during, or after administration of a drug useful in treating and/or preventing multiple myeloma. The composition according to the invention can be administered at any suitable time point before, during, or after the administration of an multiple myeloma drug or procedure (e.g., a procedure such as a stem cell transplant), or the composition according to the invention can be combined with the multiple myeloma drug for administration.

The composition according to the invention, when co-administered with a multiple myeloma drug, can be administered before, during, or after administration of the multiple myeloma drug.

In some embodiments of the invention, the composition according to the invention can be administered weekly, bi-weekly, monthly, bi-monthly, or any other suitable interval period between dosing, and which can extend for any desirable period of time, including for up to about 1, about 2, about 3, about 4, about 5, about 6, about 7, about 8, about 9 or about 10 years or more. In some embodiments, the composition according to the invention is administered once every month for up to 6 months.

3. Pharmaceutical Formulations

Pharmaceutical compositions and medicaments may be prepared by mixing one or more compounds of the invention, prodrugs thereof, pharmaceutically acceptable salts or solvates thereof, stereoisomers thereof, tautomers thereof, or solvates thereof, with pharmaceutically acceptable carriers, excipients, binders, diluents or the like to prevent and treat disorders associated with cannabinoid receptors.

The compounds and compositions of the invention may be used to prepare formulations and medicaments that prevent or treat a variety of disorders associated with cannabinoid receptors, as described herein. For example, disorders and diseases such as obesity, smoking addiction, cardimetabolic risk factors, and other disorder and diseases associated with the central nervous system can be treated using the methods, compounds, and compositions of the invention. Such compositions can be in any pharmaceutically acceptable form, such as but not limited to in the form of, for example, granules, powders, tablets, capsules, syrup, suppositories, injections, emulsions, elixirs, suspensions or solutions. The compositions can be formulated for any pharmaceutically acceptable route of administration, such as for example, by oral, parenteral, pulmonary, topical, rectal, nasal, vaginal administration, or via implanted reservoir. The dosage forms described herein are given by way of example and should not be construed as limiting the invention.

Pharmaceutically acceptable salts of the invention compounds are considered within the scope of the present invention. The compounds of the invention have a number of basic nitrogen groups, and as such, pharmaceutically acceptable salts can be formed with inorganic acids (such as hydrochloric acid, hydroboric acid, nitric acid, sulfuric acid, and phosphoric acid), organic acids (e.g. formic acid, acetic acid, trifluoroacetic acid, fumaric acid, oxalic acid, tartaric acid, lactic acid, maleic acid, citric acid, succinic acid, malic acid, methanesulfonic acid, benzenesulfonic acid, and p-toluenesulfonic acid) or acidic amino acids (such as aspartic acid and glutamic acid). The compounds of the present invention may have acidic substituent groups, and in such cases, it can form salts with metals, such as alkali and earth alkali metals (e.g. $Na^+$, $Li^+$, $K^+$, $Ca^{2+}$, $Mg^{2+}$, $Zn^{2+}$) organic amines (e.g. ammonia, trimethylamine, triethylamine, pyridine, picoline, ethanolamine, diethanolamine, triethanolamine) or basic amino acids (e.g. arginine, lysine and ornithine).

Certain compounds within the scope of the invention are derivatives referred to as prodrugs. The expression "prodrug" denotes a derivative of a known direct acting drug, e.g. esters and amides, which derivative has enhanced delivery characteristics and therapeutic value as compared to the drug, and is transformed into the active drug by an enzymatic or chemical process; see Notari, R. E., "Theory and Practice of Prodrug Kinetics," *Methods in Enzymology,* 112: 309-23 (1985); Bodor, N., "Novel Approaches in Prodrug Design," *Drugs of the Future,* 6: 165-82 (1981); and Bundgaard, H., "Design of Prodrugs: Bioreversible-Derivatives for Various Functional Groups and Chemical Entities," in DESIGN OF PRODRUGS (H. Bundgaard, ed.), Elsevier (1985), and Goodman and Gilmans, *The Pharmacological Basis Of Therapeutics,* 8th ed., McGraw-Hill (1992).

For oral, buccal, and sublingual administration, powders, suspensions, granules, tablets, pills, capsules, gelcaps, and caplets are acceptable as solid dosage forms. These can be prepared, for example, by mixing one or more compounds of the present invention, or pharmaceutically acceptable salts or tautomers thereof, with at least one additive such as a starch or other additive. Suitable additives include any pharmaceutically acceptable excipient, including but not limited to sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can comprise other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

4. Definitions

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. and Drug administration.

By "patient" is meant any animal for which treatment is desirable. Patients may be mammals, and typically, as used herein, a patient is a human individual.

The term "pharmaceutically acceptable salt," as used herein, represents salts or zwitterionic forms of the compounds of the present invention which are water or oil-soluble or dispersible; which are suitable for treatment of diseases without undue toxicity, irritation, and allergic-response; which are commensurate with a reasonable benefit/risk ratio; and which are effective for their intended use. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylene-sulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form pharmaceutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

The term "solvates" is used in its broadest sense. For example, the term solvates includes hydrates formed when a compound of the present invention contains one or more bound water molecules.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

This invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

5. WORKING EXAMPLES

General

Binding assay. The bioassay is carried out using the Perkin Elmer 96-well Top Counter. This bioassay is also known as a competition binding assay and the biological evaluation is to determine the CB receptor binding affinity ($K_i$) of the screened ligands by displacing [$^3$H]-CP-55940 (or other radioligands). The brief procedure is given below.

Perkin Elmer 96-well TopCounter is used at PMLSC and in our laboratory to determine the CB receptor binding affinity ($K_i$) of the in-silico screened ligands by displacing [$^3$H]-CP-55,940 (or other radioligands). In competition binding experiments, the tested compound dilutions are carried out in triplicate in TME buffer (25 mM Tris, 5 mM $MgCl_2$, 1 mM EDTA) containing 0.1% (w/v) fatty acid free bovine serum albumin (BSA), pH 7.4. Various concentrations of the tested compound are added in the same volume to 0.5 nM [$^3$H]CP-55,940. TME buffer and cell membrane preparations expressing CB receptors (2.5 μg per well) are added to a final volume of 200 μL. For the saturation binding experiments, varying concentrations of [$^3$H]CP-55,940 (0.05-1.5 nM) with or without 2 μM of unlabeled ligands (CP-55,940 or WIN-55,212-2) are incubated with the receptor membrane preparations to determine Kd and nonspecific binding. After the binding suspensions are incubated at 30° C. for 1 hr, the reaction is terminated by rapid filtration through microfiltration plates coated with 0.5% polyethylenimine (Unifilter GF/B filterplate, PerkinElmer) followed by 5 washes with ice cold TME buffer containing 0.5% BSA on a Packard Filtermate Harvester (PerkinElmer). The plates are then dried overnight and 30 μl MicroScint 0 scintillation cocktail are added to each well of the dried filter plates. Then the bound radioactivity is counted using a Perkin Elmer 96-well TopCounter. The $K_i$ is calculated by using nonlinear regression analysis (Prism 5; GraphPad Software Inc., San Diego, Calif.), with the Kd values for [$^3$H]CP-55,940 determined from saturation binding experiments. This assay is used for determining binding affinity parameters ($K_i$) of ligand-receptor interactions for the CB receptor.

Cyclic adenosine monophosphate (cAMP) assay: Cyclic AMP levels were measured by performing the cell-based LANCE cAMP-384 kit assay (PerkinElmer) as previously described (Yang et al., "Lead Discovery, Chemistry Optimization, and Biological Evaluation Studies of Novel Biamide Derivatives as CB(2) Receptor Inverse Agonists and Osteoclast Inhibitors," *J Med Chem.*, 55(22):9973-9987 (2012); Zhang et al., "Mutagenesis and computer modeling studies of a GPCR conserved residue W5.43(194) in ligand recognition and signal transduction for CB2 receptor," *Int. Immunopharmacol.*, 11(9):1303-1310 (2011). The assay is based on the competition between the europium-labeled cAMP tracer complex and sample cAMP for binding sites on cAMP-specific antibodies. The antibodies are labeled with Alexa Fluor dye that is sensitive to energy emissions. Briefly, the cell-based LANCE cAMP assays were performed on 384-well ProxiPlates using CHO cells stably expressing the CB2 receptors at density of 2×103 cells per well in 5 μL of RPMI-1640 medium (Gibco Laboratories, Grand Island, N.Y.) containing 1% dialyzed FBS, 25 mM HEPES, 100 μg/ml penicillin, 100 U/ml streptomycin, and 200 μg/ml of G-471. After incubation overnight, 2.5 μL of cAMP antibody and RO20-1724 (a phosphodiesterase inhibitor) in stimulation buffer (DPBS 1×, containing 0.1% BSA) was added to each well, followed by the addition of 2.5 μL of the compound plus the forskolin complex (an adenyl cyclase activator). After incubation at room temperature for 45 minutes, 10 μL of detection buffer was added into each well. The plate was then incubated at room temperature for 1 hour. The plate was then measured in a Synergy H1 hybrid reader (BioTek) with excitation at 340 nm and emission at 665 nm. The results represent at least two independent experiments each in triplicates. EC50 values were determined by nonlinear regression dose-response curve (GraphPad Prism 5).

Chemistry. All reagents were purchased from commercial sources and used without further purification. Analytical thin-layer chromatography (TLC) was performed on $SiO_2$ plates on Alumina. Visualization was accomplished by UV irradiation at 254 nm. Preparative TLC was conducted using Preparative Silica gel TLC plates (1000 μm, 20 cm×20 cm). Flash column chromatography was performed using Biotage Isolera flash purification system. Proton and carbon NMR spectra were obtained on 400 MHz or 600 MHz NMR spectrometer. Chemical shifts are reported as δ values in parts per million (ppm) as referenced to residual solvent. $^1$H NMR spectra are tabulated as follows: chemical shift, multiplicity (s=singlet, bs=broad singlet, d=doublet, t=triplet, q=quartet, m=multiplet), coupling constant(s), and number of protons. Flash column chromatography was performed using SiO2 60 (particle size 0.040-0.055 mm, 230-400 mesh).

The invention is further described by reference to the following examples, which are provided for illustration only. The invention is not limited to the examples, but rather includes all variations that are evident from the teachings provided herein. All publicly available documents referenced herein, including but not limited to U.S. patents, are specifically incorporated by reference.

Example 1

(E)-N,N-diethyl-4-(((3,4,5-trimethoxybenzyl)imino) methyl)aniline (2). (3,4,5-trimethoxyphenyl)methanamine (1972 mg, 10 mmol) was added slowly to a solution of 4-(diethylamino)benzaldehyde (1770 mg, 10 mmol) and methanol (20 mL). The mixture was stirred and refluxed for 12 hours. The reaction mixture was cooled to room temperature, and the solvent was removed by evaporation under vacuum to give the crude compound 2, which was used in the next step without further purification.

Example 2

N,N-diethyl-4-(((3,4,5-trimethoxybenzyl)amino)methyl) aniline (3). The crude compound (E)-N,N-diethyl-4-(((3,4,5-trimethoxybenzyl)imino)methyl)aniline (2) was dissolved in methanol (20 mL), and NaBH$_4$ (570 mg, 15 mmol) was added. Stirring of the mixture was continued for 12 hours at room temperature. The reaction solution was poured into water and extracted with ethyl acetate (EA). The combined organic layers were washed with water and brine and then dried over Na$_2$SO$_4$. The residue was purified by flash chromatography (ethyl acetate/petroleum ether, 1:2) on silica gel to obtain the final product (3) as yellow oil (3350 mg, yield: 93%). $^1$H NMR (400 MHz, DMSO-d6) δ 7.12 (d, J=8.4 Hz, 2H), 6.65 (s, 2H), 6.62 (d, J=8.8 Hz, 2H), 3.76 (s, 6H), 3.64 (s, 3H), 3.60 (s, 2H), 3.54 (s, 2H), 1.07 (t, J=7.2 Hz, 6H). LC-MS (ESI): m/z 359.0 (M+H)$^+$.

Example 3

N-(4-(diethylamino)benzyl)-4-methoxy-N-(3,4,5-trimethoxybenzyl)benzenesulfonamide (4). The intermediate N,N-diethyl-4-(((3,4,5- trimethoxybenzyl)amino)methyl)aniline (compound 3) (358 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with 4-methoxybenzenesulfonyl chloride (206 mg, 1.0 mmol) in DCM over 30 minutes at 0° C. and then left overnight at room temperature. The reaction solution was poured into water and extracted with EA. The combined organic layers were washed with water and brine and then dried over Na$_2$SO$_4$. The mixture was filtered and the solvent was evaporated under vacuum. The residue was purified by flash chromatography (ethyl acetate/petroleum ether, 1:2) on silica gel to obtain N-(4-(diethylamino)benzyl)-4-methoxy-N-(3,4,5-trimethoxybenzyl) benzenesulfonamide (4). Yellow solid (432 mg, yield: 82%). $^1$H NMR (400 MHz, DMSO-d6) δ 7.82 (d, J=9.20 Hz, 2H), 7.14 (d, J=8.80 Hz, 2H), 6.94 (d, J=8.80 Hz, 2H), 6.54 (d, J=8.80 Hz, 2H), 6.23 (s, 2H), 4.14 (d, J=8.0 Hz, 4H), 3.86 (s, 3H), 3.59 (s, 3H), 3.58 (s, 6H), 3.31-3.28 (m, 5H), 1.05 (t, J=6.80 Hz, 6H). LC-MS (ESI): m/z 529.1 (M+H)$^+$.

Example 4

N-(4-(diethylamino)benzyl)-3-methyl-N-(3,4,5-trimethoxybenzyl)benzenesulfonamide (5). The intermediate N,N-diethyl-4-(((3,4,5-trimethoxybenzyl)amino)methyl) aniline (compound 3) (358 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with 3-methylbenzenesulfonyl chloride (190 mg, 1.0 mmol) in DCM over 30 minutes at 0° C. and then left overnight at room temperature. The reaction solution was poured into water and extracted with EA. The combined organic layers were washed with water and brine and then dried over Na$_2$SO$_4$. The mixture was filtered and the solvent was evaporated in vacuum. The residue was purified by flash chromatography (ethyl acetate/petroleum ether, 1:2) on silica gel to obtain N-(4-(diethylamino)benzyl)-3-methyl-N-(3,4,5-trimethoxybenzyl)benzenesulfonamide (5). Yellow solid (331 mg, yield: 64.5%). $^1$H NMR (400 MHz, DMSO-d$_6$) δ 7.68-7.64 (m, 2H), 7.50 (d, J=5.60 Hz, 1H), 7.49 (s, 1H), 6.95 (d, J=8.80 Hz, 2H), 6.55 (d, J=8.80 Hz, 2H), 6.25 (s, 2H), 4.18 (d, J=8.0 Hz, 4H), 3.59 (s, 9H), 3.31-3.27 (m, 4H), 2.39 (s, 3H), 1.06 (t, J=7.20 Hz, 6H). LC-MS (ESI): m/z 513.3(M+H)$^+$.

Example 5

N-(4-(diethylamino)benzyl)-4-methyl-N-(3,4,5-trimethoxybenzyl)benzenesulfonamide (6). The intermediate N,N-diethyl-4-(((3,4,5-trimethoxybenzyl)amino)methyl) aniline (compound 3) (358 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with 4-methylbenzenesulfonyl chloride (190 mg, 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated under vacuum. The residue was purified by flash chromatography (ethyl acetate/petroleum ether, 1:2) on silica gel to obtain N-(4-(diethylamino)benzyl)-4-methyl-N-(3,4,5-trimethoxybenzyl) benzenesulfonamide (6). Yellow solid (322 mg, yield: 62%). $^1$H NMR (400 MHz, DMSO-d6) δ 7.77 (d, J=8.4 Hz, 2H), 7.43 (d, J=8.0 Hz, 2H), 6.95 (d, J=8.8 Hz, 2H), 6.54 (d, J=8.8 Hz, 2H), 6.21 (s, 2H), 4.15 (d, J=8.4 Hz, 4H), 3.59 (s, 3H), 3.58 (s, 6H), 3.30-3.26 (m, 4H), 2.42 (s, 3H), 1.06 (t, J=7.20 Hz, 6H). LC-MS (ESI): m/z 513.3 (M+H)$^+$.

Example 6

N-(4-(diethylamino)benzyl)-N-(3,4,5-trimethoxybenzyl) benzenesulfonamide (7). The intermediate N,N-diethyl-4-(((3,4,5-trimethoxybenzyl)amino)methyl)aniline (compound 3) (358 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with benzenesulfonyl chloride (176 mg, 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated under vacuum. The residue was purified by flash chromatography (ethyl acetate/petroleum ether, 1:2) on silica gel to obtain N-(4-(diethylamino)benzyl)-N-(3,4,5-trimethoxybenzyl)benzenesulfonamide (7). Brown solid (359 mg, yield: 72%). $^1$H NMR (400 MHz, DMSO-d6) δ 7.90 (d, J=7.20 Hz, 2H), 7.71-7.63 (m, 3H), 6.93 (d, J=8.80 Hz, 2H), 6.54 (d, J=8.80 Hz, 2H), 6.23 (s, 2H), 4.18 (d, J=6.80 Hz, 4H), 3.59 (s, 3H), 3.58 (s, 6H), 3.30-3.26 (m, 4H), 1.07 (t, J=7.20 Hz, 6H). LC-MS (ESI): m/z 499.1(M+H)$^+$.

Example 7

N-(4-(diethylamino)benzyl)-4-isopropyl-N-(3,4,5-trimethoxybenzyl)benzenesulfonamide (8). The intermediate N,N-diethyl-4-(((3,4,5- trimethoxybenzyl)amino)methyl)aniline(compound 3) (358 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with 4-isopropylbenzenesulfonyl chloride (218 mg 1.0 mmol), also dissolved in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated under vacuum. The residue was purified by flash chromatography (ethyl acetate/petroleum ether, 1:2) on silica gel to obtain N-(4-(diethylamino)benzyl)-4-isopropyl-N-(3,4,5-trimethoxybenzyl)benzenesulfonamide (8). Brown solid (229 mg, yield: 42%). $^1$H NMR (400 MHz, DMSO-d6) δ 7.80 (d, J=8.40 Hz, 2H), 7.49 (d, J=8.40 Hz, 2H), 6.93 (d, J=8.40 Hz, 2H), 6.54 (d, J=8.80 Hz, 2H), 6.23 (s, 2H), 4.18 (d, J=7.20 Hz, 4H), 3.59 (s, 3H), 3.58 (s, 6H), 3.31-3.26 (m, 4H), 3.04-2.98 (m, 1H), 1.25 (d, J=6.80 Hz, 6H), 1.06 (t, J=6.80 Hz, 6H). LC-MS (ESI): m/z 541.2 (M+H)$^+$.

Example 8

N-(4-(diethylamino)benzyl)-N-(3,4,5-trimethoxybenzyl) naphthalene-2-sulfonamide (9). The intermediate N,N-diethyl-4-(((3,4,5-trimethoxybenzyl)amino)methyl)aniline (compound 3) (358 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with 4-isopropylbenzenesulfonyl chloride (218 mg 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated under vacuum. The residue was purified by flash chromatography (ethyl acetate/petroleum ether, 1:2) on silica gel to obtain N-(4-(diethylamino)benzyl)-N-(3,4,5-trimethoxybenzyl)naphthalene-2-sulfonamide (9). Yellow solid (454 mg, yield: 82%). $^1$H NMR (400 MHz, DMSO-d6) δ 8.52 (s, 1H), 8.16 (t, J=8.4 Hz, 2H), 8.07, (d, J=8.0 Hz, 1H), 7.91 (d, J=1.6 Hz, 1H), 7.89-7.67 (m, 2H), 6.98 (d, J=8.8 Hz, 2H), 6.53 (d, J=8.8 Hz, 2H), 6.22 (s, 2H), 4.26 (s, 2H), 4.25 (s, 2H), 3.54 (s, 3H), 3.49 (s, 6H), 3.33-3.27 (m, 4H), 1.05 (t, J=4.4 Hz, 6H). LC-MS (ESI): m/z 549.1 (M+H)$^+$.

Example 9

N-(4-(diethylamino)benzyl)-N-(3,4,5-trimethoxybenzyl)-[1,1'-biphenyl]-4-sulfonamide (10). The intermediate N,N-diethyl-4-(((3,4,5-trimethoxybenzyl)amino)methyl)aniline (compound 3) (358 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with 4-isopropylbenzenesulfonyl chloride (218 mg 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated under vacuum. The residue was purified by flash chromatography (ethyl acetate/petroleum ether, 1:2) on silica gel to obtain N-(4-(diethylamino)benzyl)-N-(3,4,5-trimethoxybenzyl)-[1,1'-biphenyl]-4-sulfonamide (10). Yellow solid (365 mg, yield: 63%). $^1$H NMR (400 MHz, DMSO-d6) δ 7.97-7.89 (m, 4H), 7.75 (d, J=7.2 Hz, 2H), 7.56-7.47 (m, 3H), 6.98 (d, J=8.8 Hz, 2H), 6.55 (d, J=8.8 Hz, 2H), 6.25 (s, 2H), 4.23 (d, J=7.6 Hz, 4H), 3.57 (s, 9H), 3.27-3.26 (m, 4H), 1.05 (t, J=6.8 Hz, 6H). LC-MS (ESI): m/z 575.1 (M+H)$^+$.

Example 10

N-(4-(diethylamino)benzyl)-N-(3,4,5-trimethoxybenzyl) thiophene-2-carboxamide (11). The intermediate N,N-diethyl-4-(((3,4,5-trimethoxybenzyl)amino)methyl)aniline (compound 3) (358 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with thiophene-2-carbonyl chloride (146 mg 1.0 mmol), also dissolved in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated under vacuum. The residue was purified by flash chromatography (ethyl acetate/petroleum ether, 1:2) on silica gel to obtain N-(4-(diethylamino)benzyl)-N-(3,4,5-trimethoxybenzyl)thiophene-2-carboxamide (11). Yellow oil (363 mg, yield: 77%). $^1$H NMR (400 MHz, CDCl3) δ 7.76 (s, 1H), 7.49 (t, J=6.8 Hz, 2H), 7.35 (s, 1H), 7.15 (s, 1H), 7.015 (s. 1H), 6.70 (s, 1H), 6.49 (s, 2H), 4.67 (t, J=9.6 Hz, 4H), 3.86 (s, 9H), 3.38 (d, J=6.8 Hz, 3H), 3.15 (t, J=5.2 Hz, 1H), 1.07 (d, J=5.6 Hz, 6H). LC-MS (ESI): m/z 469.4 (M+H)$^+$.

Example 11

N-(4-(diethylamino)benzyl)-N-(3,4,5-trimethoxybenzyl) quinoxaline-2-carboxamide (12). The intermediate N,N-diethyl-4-(((3,4,5-trimethoxybenzyl)amino)methyl)aniline (compound 3) (358 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with quinoxaline-2-carbonyl chloride (192 mg 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated under vacuum. The residue was purified by flash chromatography (ethyl acetate/petroleum ether, 1:2) on silica gel to obtain N-(4-(diethylamino)benzyl)-N-(3,4,5-trimethoxybenzyl)quinoxaline-2-carboxamide (12). Yellow oil (400 mg, yield: 77%). $^1$H NMR (400 MHz, DMSO-d6) δ 8.92 (s, 1H), 8.16-8.09 (m, 2H), 7.98-7.93 (m, 2H), 7.27 (d, J=8.8 Hz, 1H), 7.10 (d, J=8.8 Hz, 1H), 6.70-6.58 (m, 3H), 6.25 (s, 1H), 4.62-4.49 (m, 4H), 1.052 (t, J=3.6 Hz, 6H). LC-MS (ESI): m/z 515.2 (M+H)$^+$.

Example 12

N-(4-(diethylamino)benzyl)-4-(trifluoromethoxy)-N-(3,4,5-trimethoxybenzyl)benzenesulfonamide (13). The intermediate N,N-diethyl-4-(((3,4,5-trimethoxybenzyl)amino)methyl)aniline (compound 3) (358 mg, 1.0 mmol) in dichloromethane (DCM, 10 mL) was chilled in ice bath with the exclusion of moisture, and then triethylamine (TEA, 121 mg, 1.2 mmol) was added to it. The resulting solution was treated drop-wise under stirring with 4-(trifluoromethoxy)benzenesulfonyl chloride (260 mg, 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated under vacuum. The residue was purified by flash chromatography (ethyl acetate/petroleum ether, 1:2) on silica gel to obtain N-(4-(diethylamino)benzyl)-4-(trifluoromethoxy)-N-(3,4,5-trimethoxybenzyl)benzenesulfonamide (13). Yellow solid (455 mg, yield: 78%). $^1$H NMR (400 MHz, DMSO-d6) δ 8.0 (d, J=8.80 Hz, 2H), 7.59 (d, J=8.0 Hz, 2H), 6.94 (d, J=8.8 Hz, 2H), 6.54 (d, J=8.8 Hz, 2H), 6.27 (s, 2H), 4.23 (d, J=7.6 Hz, 4H), 3.60 (s, 6H), 3.59 (s, 3H), 3.30-3.25 (m, 4H), 1.06 (t, J=7.2 Hz, 6H). LC-MS (ESI): m/z 583.1 (M+H)$^+$.

Example 13

N-(4-(diethylamino)benzyl)-2-methyl-N-(3,4,5-trimethoxybenzyl)benzenesulfonamide (14). The intermediate N,N-diethyl-4-(((3,4,5-trimethoxybenzyl)amino)methyl) aniline (compound 3) (358 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with 2-methylbenzenesulfonyl chloride (190 mg, 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated in vacuum. The residue was purified by flash chromatography (ethyl acetate/petroleum ether, 1:2) on silica gel to obtain N-(4-(diethylamino)benzyl)-2-methyl-N-(3,4,5-trimethoxybenzyl)benzenesulfonamide (14). Yellow solid (216 mg, yield: 42%). $^1$H NMR (400 MHz, DMSO-d6) δ 7.90 (d, J=6.8 Hz, 1H), 7.59 (t, J=6.4 Hz, 1H), 7.49-7.40 (m, 2H), 6.94 (d, J=8.8 Hz, 2H), 6.54 (d, J=8.8 Hz, 2H), 6.27 (s, 2H), 4.22 (s, 2H), 4.19 (s, 2H), 3.62 (s, 6H), 3.61 (3H), 3.30-3.28 (m, 4H), 2.56 (s, 3H), 1.07 (t, J=6.8 Hz, 6H). LC-MS (ESI): m/z 513.1 (M+H)$^+$.

Example 14

(E)-N-(4-(diethylamino)benzyl)-2-phenyl-N-(3,4,5-trimethoxybenzyl)ethene-1-sulfonamidebenzenesulfonamide (15). The intermediate N,N-diethyl-4-(((3,4,5-trimethoxybenzyl)amino)methyl) aniline (compound 3) (358 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with (E)-2-phenylethene-1-sulfonyl chloride (202 mg, 1.0 mmol), also dissolved in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated under vacuum. The residue was purified by flash chromatography (ethyl acetate/petroleum ether, 1:2) on silica gel to obtain (E)-N-(4-(diethylamino)benzyl)-2-phenyl-N-(3,4,5-trimethoxybenzyl)ethene-1-sulfonamidebenzenesulfonamide (15). White solid (278 mg, yield: 53%). $^1$H NMR (400 MHz, DMSO-d6) δ 7.65 (t, J=2.4 Hz, 2H), 7.44-7.42 (m, 3H), 7.38 (s, 1H), 7.26 (s, 1H), 7.09 (d, J=8.80 Hz, 2H), 6.59 (d, J=8.40 Hz, 2H), 6.47 (s, 2H), 4.22 (s, 2H), 4.19 (s, 2H), 3.65 (s, 6H), 3.59 (s, 3H), 3.30-3.25 (m, 4H), 1.06 (t, J=7.20 Hz, 6H). 1H NMR (400 MHz, CDCl3) δ 7.44-7.37 (m, 6H), 6.64 (d, J=8.80 Hz, 2H), 6.56-6.502 (m, 3H), 4.28 (s, 4H), 3.85 (s, 3H), 3.82 (s, 6H), 1.18 (t, J=6.80 Hz, 6H). LC-MS (ESI): m/z 525.2 (M+H)$^+$.

Example 15

N-(4-(diethylamino)benzyl)-N-(3,4,5-trimethoxybenzyl) thiophene-2-sulfonamide (16). The intermediate N,N-diethyl-4-(((3,4,5-trimethoxybenzyl)amino)methyl)aniline (compound 3) (358 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with thiophene-2-sulfonyl chloride (182 mg, 1.0 mmol) in DCM over 30 minutes at 0° C. and then left overnight at room temperature. The reaction solution was poured into water and extracted with EA. The combined organic layers were washed with water and brine and then dried over Na$_2$SO$_4$. The mixture was filtered and the solvent was evaporated under vacuum. The residue was purified by flash chromatography (ethyl acetate/petroleum ether, 1:2) on silica gel to obtain N-(4-(diethylamino)benzyl)-N-(3,4,5-trimethoxybenzyl)thiophene-2-sulfonamide (16). Yellow solid (270 mg, yield: 54%). $^1$H NMR (400 MHz, DMSO-d6) δ 8.03-8.02 (m, 1H), 7.76-7.75 (m, 1H), 7.28-7.25 (m, 1H), 6.96 (d, J=8.40 Hz, 2H), 6.55 (d, J=8.80 Hz, 2H), 6.28 (s, 2H), 4.20 (s, 2H), 4.17 (s, 2H), 3.61 (s, 6H), 3.60 (s, 3H), 3.30-3.26 (m, 4H), 1.06 (t, J=11.20 Hz, 6H). LC-MS (ESI): m/z 505.5 (M+H)$^+$.

Example 16

N-(4-(diethylamino)benzyl)-3,4-dimethoxy-N-(3,4,5-trimethoxybenzyl)benzenesulfonamide (17). The intermediate N,N-diethyl-4-(((3,4,5-trimethoxybenzyl)amino)methyl)aniline (compound 3) (358 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with 3,4-dimethoxybenzenesulfonyl chloride (236 mg, 1.0 mmol) in DCM over 30 minutes at 0° C. and then left overnight at room temperature. The reaction solution was poured into water and extracted with EA. The combined organic layers were washed with water and brine and then dried over Na$_2$SO$_4$. The mixture was filtered and the solvent was evaporated under vacuum. The residue was purified by flash chromatography (ethyl acetate/petroleum ether, 1:2) on silica gel to obtain N-(4-(diethylamino)benzyl)-3,4-dimethoxy-N-(3,4,5-trimethoxybenzyl)benzenesulfonamide (17). Brown oil (436 mg, yield: 78%). $^1$H NMR (400 MHz, DMSO-d6) δ 7.49 (d, J=2.4 Hz, 1H), 7.47 (s, 1H), 7.46-7.223 (m, 1H), 7.15 (d, J=8.80 Hz, 2H), 6.55 (d, J=8.80 Hz, 2H), 6.25 (s, 2H), 4.18 (s, 2H), 4.17 (s, 2H), 3.86 (s, 3H), 3.79 (s, 3H), 3.79 (s, 6H), 3.59 (s, 3h), 3.31-3.28 (m, 4H), 1.06 (t, J=7.20 Hz, 6H). LC-MS (ESI): m/z 559.4 (M+H)$^+$.

Example 17

N-(4-(diethylamino)benzyl)-4-formyl-N-(3,4,5-trimethoxybenzyl)benzenesulfonamide (18). The intermediate N,N-diethyl-4-(((3,4,5-trimethoxybenzyl)amino)methyl)aniline (compound 3) (358 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with 4-formylbenzenesulfonyl chloride (204 mg, 1.0 mmol) in DCM over 30 minutes at 0° C. and then left overnight at room temperature. The reaction solution was poured into water and extracted with EA. The combined organic layers were washed with water and brine and then dried over Na$_2$SO$_4$. The mixture was filtered and the solvent was evaporated under vacuum. The residue was purified by flash chromatography (ethyl acetate/petroleum ether, 1:2) on silica gel to obtain N-(4-(diethylamino)benzyl)-4-formyl-N-(3,4,5-trimethoxybenzyl) benzenesulfonamide (18). Yellow solid (374 mg, yield: 71%). $^1$H NMR (400 MHz, DMSO-d6) δ 10.13 (s, 1H), 8.11-8.06 (m, 4H), 6.95 (d, J=8.80 Hz, 2H), 6.53 (d, J=8.40 Hz, 2H), 6.26 (s, 2H), 4.24 (t, J=7.20 Hz, 4H), 3.59 (s, 9H), 3.30-3.26 (m, 4H), 1.05 (t, J=6.80 Hz, 6H). 1H NMR (600 MHz, CDCl3) δ 7.99 (d, J=1.80 Hz, 4H), 6.86 (d, J=9.0 Hz, 2H), 6.49 (d, J=8.40 Hz, 2H), 6.30 (s, 2H), 4.30 (s, 2H), 4.27 (s, 2H), 3.81 (s, 3H), 3.72 (s, 6H), 1.13 (t, J=7.20 Hz, 6H). LC-MS (ESI): m/z 527.4 (M+H)$^+$.

Example 18

(E)-N,N-diethyl-4-(((pyridin-3-ylmethyl)imino)methyl)aniline (19). Pyridin-3-ylmethanamine (1081 mg, 10 mmol) was added slowly to a solution of 4-(diethylamino)benzaldehyde (1770 mg, 10 mmol) and methanol (20 mL). The reaction mixture was stirred and refluxed for 12 hours. The reaction mixture was cooled to room temperature, and the solvent was removed by evaporation under vacuum to give the crude compound 19, which was used in the next step without further purification.

Example 19

N,N-diethyl-4-(((pyridin-3-ylmethyl)amino)methyl)aniline (20). The crude compound (E)-N,N-diethyl-4-(((pyridin-3-ylmethyl)imino)methyl)aniline (19) was dissolved in methanol (20 mL), and NaBH4 (570 mg, 15 mmol) was added. Stirring of the mixture was continued for 12 hours at room temperature. The reaction solution was poured into water and extracted with EA. The combined organic layers were washed with water and brine and then dried over Na$_2$SO$_4$. The residue was purified by flash chromatography (methanol/DCM, 1:9) on silica get to obtain the final product (20). Yellow oil (1140 mg, yield: 84%). $^1$H NMR (400 MHz, DMSO-d6) δ 8.52 (s, 1H), 8.51-8.43 (m, 1H), 7.76-7.32 (m, 1H), 7.36-7.32 (m, 1H), 7.11 (d, J=8.40 Hz, 2H), 6.61 (d, J=8.80 Hz, 2H), 3.68 (s, 2H), 3.54 (s, 2H), 3.31-3.28 (m, 4H), 2.85 (s, 1H), 1.07 (t, J=6.80 Hz, 6H). LC-MS (ESI): m/z 270.2 (M+H)$^+$.

Example 20

N-(4-(diethylamino)benzyl)-N-(pyridin-3-ylmethyl)thiophene-2-carboxamide (21). The intermediate N,N-diethyl-4-(((pyridin-3-ylmethyl)amino)methyl)aniline (compound 20) (269 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with thiophene-2-carbonyl chloride (156 mg, 1.0 mmol) in DCM over 30 minutes at 0° C. and then left overnight at room temperature. The reaction solution was poured into water and extracted with EA. The combined organic layers were washed with water and brine and then dried over Na$_2$SO$_4$. The mixture was filtered and the solvent was evaporated under vacuum. The residue was purified by flash chromatography (ethyl acetate/petroleum ether, 1:2) on silica gel to obtain N-(4-(diethylamino)benzyl)-N-(pyridin-3-ylmethyl)thiophene-2-carboxamide (21). Dark brown oil (342 mg, yield: 90%). $^1$H NMR (400 MHz, DMSO-d6) δ 8.50-8.47 (m, 2H), 7.78 (d, J=4.40 Hz, 1H), 7.77-7.66 (m, 1H), 7.39-7.36 (m, 2H), 7.11-7.04 (m, 3H), 6.65 (d, J=8.40 Hz, 2H), 4.62 (d, J=12.40 Hz, 4H), 3.31-3.28 (m, 4H), 1.08 (t, J=6.80 Hz, 6H). LC-MS (ESI): m/z 380.0 (M+H)$^+$.

Example 21

N-(4-(diethylamino)benzyl)-N-(pyridin-3-ylmethyl)quinoxaline-2-carboxamide (22). The intermediate N,N-diethyl-4-(((pyridin-3-ylmethyl)amino)methyl)aniline (compound 20) (269 mg, 1.0 mmol) in dichloromethane (DCM, 10 mL) was chilled in an ice bath with the exclusion of moisture, and then triethylamine (TEA, 121 mg, 1.2 mmol)

was added to it. The resulting solution was treated drop-wise under stirring with quinoxaline-2-carbonyl chloride (192 mg, 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated under vacuum. The residue was purified by flash chromatography (ethyl acetate/petroleum ether, 1:2) on silica gel to obtain N-(4-(diethylamino)benzyl)-N-(pyridin-3-ylmethyl)quinoxaline-2-carboxamide (22). Yellow solid (305 mg, yield: 72%). $^1$H NMR (400 MHz, DMSO-d6) δ 9.17 (s, 1H), 8.57 (d, J=1.60 Hz, 1H), 8.52-8.51 (m, 1H), 8.48-8.43 (m, 1H), 8.18-8.14 (m, 1H), 7.99-7.91 (m, 2H), 7.80-7.76 (m, 1H), 4.68 (s, 2H), 4.57 (s, 1H), 4.53 (s, 1H), 3.37-3.28 (m, 4H), 1.06 (t, J=7.20 Hz, 6H). LC-MS (ESI): m/z 426.1 (M+H)$^+$.

Example 22

(E)-N-(4-(diethylamino)benzyl)-2-phenyl-N-(pyridin-3-ylmethyl)ethene-1-sulfonamide (23). The intermediate N,N-diethyl-4-(((pyridin-3-ylmethyl)amino)methyl)aniline (compound 20) (269 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with (E)-2-phenylethene-1-sulfonyl chloride (202 mg, 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated in vacuum. The residue was purified by flash chromatography (ethyl acetate/petroleum ether, 1:2) on silica gel to obtain (E)-N-(4-(diethylamino)benzyl)-2-phenyl-N-(pyridin-3-ylmethyl)ethene-1-sulfonamide (23). Brown solid (270 mg, yield: 62%). $^1$H NMR (400 MHz, DMSO-d6) δ 8.43-8.41 (m, 2H), 7.66-7.61 (m, 3H), 7.454-7.43 (m, 3H), 7.42 (s, 1H), 7.31-7.27 (m, 1H), 7.28 (s, 1H), 7.07 (d, J=8.80 Hz, 2H), 4.31 (s, 2H), 4.20 (s, 2H), 3.31-3.26 (m, 4H), 1.05 (t, J=6.80 Hz, 6H). LC-MS (ESI): m/z 436.2 (M+H)$^+$.

Example 23

N-(4-(diethylamino)benzyl)-N-(pyridin-3-ylmethyl)naphthalene-2-sulfonamide (24). The intermediate N,N-diethyl-4-(((pyridin-3-ylmethyl)amino)methyl)aniline (compound 20) (269 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with naphthalene-2-sulfonyl chloride (226 mg, 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated under vacuum. The residue was purified by flash chromatography (ethyl acetate/petroleum ether, 1:2) on silica gel to obtain N-(4-(diethylamino)benzyl)-N-(pyridin-3-ylmethyl)naphthalene-2-sulfonamide (24). Brown solid (285 mg, yield: 62%). $^1$H NMR (400 MHz, DMSO-d6) δ 8.51 (s, 1H), 8.36 (d, J=1.60 Hz, 1H), 8.28 (s, 1H), 8.18-8.14 (m, 2H), 8.09 (d, J=7.60 Hz, 1H), 7.88 (dd, J1=2.0 Hz, J2=8.80 Hz, 2H), 7.76-7.70 (m, 3H), 7.22-7.18 (m, 1H), 6.91 (d, J=8.80 Hz, 2H), 6.45 (d, J=8.80 Hz, 2H), 4.35 (s, 2H), 4.24 (s, 2H), 3.27-3.24 (m, 4H), 1.02 (t, J=7.20 Hz, 6H). LC-MS (ESI): m/z 460.3 (M+H)$^+$.

Example 24

N-(4-(diethylamino)benzyl)-N-(pyridin-3-ylmethyl)-[1,1'-biphenyl]-4-sulfonamide (25). The intermediate N,N-diethyl-4-(((pyridin-3-ylmethyl)amino)methyl)aniline (compound 20) (269 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with [1,1'-biphenyl]-4-sulfonyl chloride (252 mg, 1.0 mmol), also dissolved in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated under vacuum. The residue was purified by flash chromatography (ethyl acetate/petroleum ether, 1:2) on silica gel to obtain N-(4-(diethylamino)benzyl)-N-(pyridin-3-ylmethyl)-[1,1'-biphenyl]-4-sulfonamide (25). Yellow solid (273 mg, yield: 56%). $^1$H NMR (400 MHz, DMSO-d6) δ 8.38-8.37 (m, 1H), 8.28 (d, J=1.60 Hz, 1H), 7.96-7.90 (m, 4H), 7.79-7.77 (m, 2H), 7.57-7.53 (m, 2H), 7.49-7.45 (m, 2H), 7.23-7.19 (m, 1H), 6.91 (d, J=8.80 Hz, 2H), 6.48 (d, J=8.80 Hz, 2H), 4.32 (s, 2H), 4.22 (s, 2H), 3.29-3.25 (m, 4H), 1.03 (t, J=6.80 Hz, 6H). LC-MS (ESI): m/z 485.7 (M+H)$^+$.

Example 25

4-(((benzo[d][1,3]dioxol-5-ylmethyl)amino)methyl)-N,N-diethylaniline (27). Benzo[d][1,3]dioxol-5-ylmethanamine (1511 mg, 10 mmol) was added slowly to a solution of 4-(diethylamino)benzaldehyde (1770 mg, 10 mmol) and methanol (20 mL). The reaction mixture was stirred and refluxed for 12 hours. The reaction mixture was cooled to room temperature, and the solvent was removed by evaporation in vacuum to give the crude compound 27, which was used in the next step without further purification.

Example 26

4-(((benzo[d][1,3]dioxol-5-ylmethyl)amino)methyl)-N,N-diethylaniline (28). The crude compound (Z)-4-(((benzo[d][1,3]dioxol-5-ylmethyl)imino)methyl)-N,N-diethylaniline (27) was dissolved in methanol (20 mL), and NaBH4 (570 mg, 15 mmol) was added. Stirring of the mixture was continued for 12 hours at room temperature. The reaction solution was poured into water and extracted with EA. The combined organic layers were washed with water and brine and then dried over $Na_2SO_4$. The residue was purified by flash chromatography (ethyl acetate/petroleum ether, 1:2) on silica get to obtain the final product (28). Yellow oil (2900 mg, yield: 92%). $^1$H NMR (400 MHz, DMSO-d6) δ 7.09 (d, J=8.40 Hz, 2H), 6.92 (s, 1H), 6.92-6.78 (m, 1H), 6.76 (d, J=8.80 Hz, 2H), 5.98 (s, 2H), 3.57 (s, 2H), 3.50 (s, 2H), 3.31-3.27 (m, 4H), 1.07 (t, J=7.20 Hz, 6H). LC-MS (ESI): m/z 313.3 (M+H)$^+$.

Example 27

(E)-N-(benzo[d][1,3]dioxol-5-ylmethyl)-N-(4-(diethylamino)benzyl)-2-phenylethene-1-sulfonamide (29). The intermediate 4-(((benzo[d][1,3]dioxol-5-ylmethyl)amino)

methyl)-N,N-diethylaniline (compound 28) (312 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with (E)-2-phenylethene-1-sulfonyl chloride (202 mg, 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated under vacuum. The residue was purified by flash chromatography (ethyl acetate/petroleum ether, 1:2) on silica gel to obtain (E)-N-(benzo[d][1,3]dioxol-5-ylmethyl)-N-(4-(diethylamino)benzyl)-2-phenylethene-1-sulfonamide (29). White solid (100 mg, yield: 20%). $^1$H NMR (400 MHz, DMSO-d6) δ 7.61-7.59 (m, 2H), 7.43 (s, 2H), 7.42 (s, 1H), 7.31 (s, 1H), 7.11 (s, 1H), 7.07 (t, J=4.80 Hz, 2H), 6.84 (d, J=7.60 Hz, 1H), 6.81 (s, 1H), 6.76 (d, J=7.60 Hz, 1H), 6.58 (d, J=8.80 Hz, 2H), 5.96 (s, 2H), 4.15 (d, J=6.40 Hz, 4H), 3.31-3.27 (m, 4H), 1.05 (t, J=7.20 Hz, 6H). LC-MS (ESI): 479.4 (M+H)$^+$.

Example 28

N-(benzo[d][1,3]dioxol-5-ylmethyl)-N-(4-(diethylamino)benzyl)-4-formylbenzenesulfonamide (30). The intermediate 4-(((benzo[d][1,3]dioxol-5-ylmethyl)amino)methyl)-N,N-diethylaniline (compound 28) (312 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with 4-formylbenzenesulfonyl chloride (204 mg, 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated in vacuum. The residue was purified by flash chromatography (ethyl acetate/petroleum ether, 1:2) on silica gel to obtain N-(benzo[d][1,3]dioxol-5-ylmethyl)-N-(4-(diethylamino)benzyl)-4-formylbenzenesulfonamide (30). Yellow solid (410 mg, yield: 85%). $^1$H NMR (400 MHz, DMSO-d6) δ 10.13 (s, 1H), 8.07 (d, J=8.40 Hz, 2H), 8.01 (d, J=8.40 Hz, 2H), 6.86 (d, J=8.80 Hz, 2H), 6.78 (d, J=8.0 Hz, 1H), 6.62-6.57 (m, 1H), 6.57 (s, 1H), 6.49 (d, J=8.80 Hz, 2H), 5.95 (s, 2H), 4.23 (s, 2H), 4.19 (s, 2H), 3.30-3.25 (m, 4H), 1.04 (t, J=7.20 Hz, 6H). LC-MS (ESI): m/z 480.2 (M+H)$^+$.

Example 29

4-(((benzo[d][1,3]dioxol-5-ylmethyl)(quinoxalin-2-ylmethyl)amino)methyl)-N,N-diethylaniline (31). The intermediate 4-(((benzo[d][1,3]dioxol-5-ylmethyl)amino)methyl)-N,N-diethylaniline (compound 28) (312 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with quinoxaline-2-carbonyl chloride (192 mg, 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated under vacuum. The residue was purified by flash chromatography (ethyl acetate/petroleum ether, 1:2) on silica gel to obtain 4-(((benzo[d][1,3]dioxol-5-ylmethyl)(quinoxalin-2-ylmethyl)amino)methyl)-N,N-diethylaniline (31). Brown oil (418 mg, yield: 89%). $^1$H NMR (600 MHz, DMSO-d6) δ 9.13 (s, 1H), 8.16-8.13 (m, 2H), 7.96-7.93 (m, 2H), 6.40-6.91 (m, 2H), 6.87-6.83 (m, 1H), 6.67 (d, J=8.40 Hz, 2H), 6.57 (d, J=8.40 Hz, 2H), 5.99 (s, 2H), 4.50 (s, 2H), 4.40 (s, 2H), 3.30-3.27 (m, 4H), 1.05 (t, J=7.20 Hz, 6H). LC-MS (ESI): m/z 469.1 (M+H)$^+$.

Example 30

N-(benzo[d][1,3]dioxol-5-ylmethyl)-N-(4-(diethylamino)benzyl)thiophene-2-carboxamide (32). The intermediate 4-(((benzo[d][1,3]dioxol-5-ylmethyl)amino)methyl)-N,N-diethylaniline (compound 28) (312 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with thiophene-2-carbonyl chloride (146 mg, 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated under vacuum. The residue was purified by flash chromatography (ethyl acetate/petroleum ether, 1:2) on silica gel to obtain N-(benzo[d][1,3]dioxol-5-ylmethyl)-N-(4-(diethylamino)benzyl)thiophene-2-carboxamide (32). Dark brown oil (290 mg, yield: 69%). $^1$H NMR (400 MHz, DMSO-d6) δ 7.78-7.76 (m, 1H), 7.33 (s, 1H), 7.09-7.07 (m, 1H), 7.04 (d, J=8.0 Hz, 2H), 6.90 (d, J=8.0 Hz, 1H), 6.82 (s, 1H), 6.73 (d, J=7.20 Hz, 1H), 6.65 (d, J=8.80 Hz, 2H), 6.02 (s, 2H), 4.52 (s, 4H), 3.36-3.02 (m, 4H), 1.08 (t, J=7.20 Hz, 6H). LC-MS (ESI): m/z 423.2 (M+H)$^+$.

Example 31

N-(benzo[d][1,3]dioxol-5-ylmethyl)-N-(4-(diethylamino)benzyl)naphthalene-2-sulfonamide (33). The intermediate 4-(((benzo[d][1,3]dioxol-5-ylmethyl)amino)methyl)-N,N-diethylaniline (compound 28) (312 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with naphthalene-2-sulfonyl chloride (226 mg, 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated in vacuum. The residue was purified by flash chromatography (ethyl acetate/petroleum ether, 1:2) on silica gel to obtain N-(benzo[d][1,3]dioxol-5-ylmethyl)-N-(4-(diethylamino)benzyl)naphthalene-2-sulfonamide (33). Yellow oil (76 mg, yield: 15%). $^1$H NMR (400 MHz, DMSO-d6) δ 8.42 (d, J=1.6 Hz, 1H), 8.14-8.11 (m, 12H), 8.07 (d, J=8.0 Hz, 1H), 7.84-7.82 (m, 1H), 7.73-7.68 (m, 2H), 6.88 (d, J=8.8 Hz, 2H), 6.75 (d, J=8.0 Hz, 1H), 6.64-6.61 (m, 1H), 6.57 (d, J=1.6 Hz, 1H), 6.47 (d, J=8.8 Hz, 2H), 5.91 (s, 2H), 4.22 (d, J=6.8 Hz, 4H), 3.29-3.23 (m, 4H), 1.02 (t, J=6.8 Hz, 6H). LC-MS (ESI): m/z 503.6 (M+H)$^+$.

Example 32

N-(benzo[d][1,3]dioxol-5-ylmethyl)-N-(4-(diethylamino)benzyl)-[1,1'-biphenyl]-4-sulfonamide (34). The intermediate 4-(((benzo[d][1,3]dioxol-5-ylmethyl)amino)methyl)-N,N-diethylaniline (compound 28) (312 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with [1,1'-biphenyl]-4-sulfonyl chloride (252 mg, 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated under vacuum. The residue was purified by flash chromatography (ethyl acetate/petroleum ether, 1:2) on silica gel to obtain N-(benzo[d][1,3]dioxol-5-ylmethyl)-N-(4-(diethylamino)benzyl)-[1,1'-biphenyl]-4-sulfonamide (34). Yellow oil (363 mg, yield: 69%). $^1$H NMR (400 MHz, DMSO-d6) δ 7.88 (d, J=2.0 Hz, 4H), 7.77-7.75 (m, 2H), 7.56-7.52 (m, 2H), 7.49-7.45 (m, 1H), 6.88 (d, J=8.4 Hz, 2H), 6.77 (d, J=8.0 Hz, 1H), 6.62-6.60 (m, 1H), 6.57 (d, J=1.6 Hz, 1H), 6.50 (d, J=8.8 Hz, 2H), 4.19 (d, J=9.6 Hz, 4H), 3.28-3.24 (m, 4H), 1.03 (t, J=7.2 Hz, 6H). LC-MS (ESI): m/z 529.1 $(M+H)^+$.

Example 33

(Z)-N,N-diethyl-4-((pentylimino)methyl)aniline (35). Pentan-1-amine (871 mg, 10 mmol) was added slowly to a solution of 4-(diethylamino)benzaldehyde (1770 mg, 10 mmol) and methanol (20 mL). The reaction mixture was stirred and refluxed for 12 hours. The reaction mixture was cooled to room temperature, and the solvent was removed by evaporation under vacuum to give the crude compound 35, which was used in the next step without further purification.

Example 34

N,N-diethyl-4-((pentylamino)methyl)aniline (36). The crude compound (Z)-N,N-diethyl-4-((pentylimino)methyl)aniline (35) was dissolved in methanol (20 mL), and $NaBH_4$ (570 mg, 15 mmol) was added. Stirring of the mixture was continued for 12 hours at room temperature. The reaction solution was poured into water and extracted with EA. The combined organic layers were washed with water and brine and then dried over $Na_2SO_4$. The residue was purified by flash chromatography (ethyl acetate/petroleum ether, 2:1) on silica get to obtain the final product (36). Yellow oil, (2450 mg, yield: 99%). $^1$H NMR (600 MHz, DMSO-d6) δ 7.08 (d, J=13.20 Hz, 2H), 6.59 (d, J=13.20 Hz, 2H), 3.52 (s, 2H), 3.31-3.27 (m, 4H), 2.47-2.43 (m, 2H), 1.42-1.39 (m, 2H0, 1.28-1.24 (m, 4H), 1.07 (t, J=10.20 Hz, 6H), 0.85 (t, J=7.80 Hz, 3H). LC-MS (ESI): m/z 249.4 $(M+H)^+$.

Example 35

(E)-N-(4-(diethylamino)benzyl)-N-pentyl-2-phenylethene-1-sulfonamide (37). The intermediate N,N-diethyl-4-((pentylamino)methyl)aniline (compound 36) (248 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with (E)-2-phenylethene-1-sulfonyl chloride (202 mg, 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated under vacuum. The residue was purified by flash chromatography (ethyl acetate/petroleum ether, 1:2) on silica gel to obtain (E)-N-(4-(diethylamino)benzyl)-N-pentyl-2-phenylethene-1-sulfonamide (37). Dark brown oil (285 mg, yield: 69%). $^1$H NMR (600 MHz, DMSO-d6) δ 7.67 (t, J=3.60 Hz, 2H), 7.43 (s, 3H), 7.34 (d, J=15.60 Hz, 1H), 7.18-7.13 (m, 2H), 6.62 (d, J=8.40 Hz, 2H), 4.18 (a, 2H), 3.29-3.05 (m, 4H), 3.03-3.02 (m, 2H), 1.41 (t, J=7.20 Hz, 2H), 1.89-1.16 (m, 4H), 1.05 (t, J=6.60 Hz, 6H), 0.76 (t, J=7.20 Hz, 3H). LC-MS (ESI): m/z 415.2 $(M+H)^+$.

Example 36

N-(4-(diethylamino)benzyl)-4-formyl-N-pentylbenzenesulfonamide (38). The intermediate N,N-diethyl-4-((pentylamino)methyl)aniline (compound 36) (248 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with 4-formylbenzenesulfonyl chloride (204 mg, 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated under vacuum. The residue was purified by flash chromatography (ethyl acetate/petroleum ether, 1:2) on silica gel to obtain N-(4-(diethylamino)benzyl)-4-formyl-N-pentylbenzenesulfonamide (38). Yellow solid (259 mg, yield: 62%). $^1$H NMR (600 MHz, DMSO-d6) δ 8.10 (d, J=8.40 Hz, 2H), 8.03 (d, J=7.80 Hz, 2H), 7.04 (d, J=8.40 Hz, 2H), 6.58 (d, J=9.0 Hz, 2H), 4.19 (s, 2H), 3.32-3.28 (m, 4H), 3.04 (t, J=7.80 Hz, 2H), 1.26 (t, J=7.20 Hz, 2H), 1.08 (t, J=6.40 Hz, 4H), 1.02 (t, J=7.20 Hz, 6H), 0.707 (t, J=7.80 Hz, 3H). LC-MS (ESI): m/z 417.7 $(M+H)^+$.

Example 37

N-(4-(diethylamino)benzyl)-N-pentylquinoxaline-2-carboxamide (39). The intermediate N,N-diethyl-4-((pentylamino)methyl)aniline (compound 35) (248 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with quinoxaline-2-carbonyl chloride (192 mg, 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated under vacuum. The residue was purified by flash chromatography (ethyl acetate/petroleum ether, 1:2) on silica gel to obtain N-(4-(diethylamino)benzyl)-N-pentylquinoxaline-2-carboxamide (39). Yellow solid (364 mg, yield: 90%). $^1$H NMR (600 MHz, DMSO-d6) δ 9.06 (s, 1H), 7.22 (d, J=9.0

Hz, 2H), 7.09 (d, J=9.0 Hz, 2H), 6.67 (d, J=8.40 Hz, 2H), 6.58 (d, J=8.40 Hz, 2H), 4.49 (s, 2H), 3.29-3.27 (m, 4H), 1.62-1.58 (m, 2H), 1.32-1.24 (m, 4H), 1.08 (t, J=7.20 Hz, 6H), 0.87 (t, J=6.60 Hz, 3H). LC-MS (ESI): m/z 405.5 (M+H)+.

Example 38

N-(4-(diethylamino)benzyl)-N-pentylthiophene-2-carboxamide (40). The intermediate N,N-diethyl-4-((pentylamino)methyl)aniline (compound 35) (248 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with thiophene-2-carbonyl chloride (146 mg, 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated under vacuum. The residue was purified by flash chromatography (ethyl acetate/petroleum ether, 1:2) on silica gel to obtain N-(4-(diethylamino)benzyl)-N-pentylthiophene-2-carboxamide (40). Dark brown solid (100 mg, Yield: 40%). $^1$H NMR (600 MHz, DMSO-d6) δ 7.74 (d, J=4.80 Hz, 1H), 7.35 (s, 1H), 7.08 (d, J=6.0 Hz, 3H), 6.65 (s, 2H), 4.58 (s, 2H), 3.34-3.31 (m, 4H), 1.98 (t, J=6.40 Hz, 2H), 1.56 (s, 2H), 1.17 (t, J=7.20 Hz, 4H), 1.07 (t, J=4.80 Hz, 6H), 0.83 (d, J=5.40 Hz, 3H). LC-MS (ESI): m/z 359.6 (M+H)+.

Example 39

N-(4-(diethylamino)benzyl)-N-pentylnaphthalene-1-sulfonamide (41). The intermediate N,N-diethyl-4-((pentylamino)methyl)aniline (compound 35) (248 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with naphthalene-2-sulfonyl chloride (226 mg, 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated in vacuum. The residue was purified by flash chromatography (ethyl acetate/petroleum ether, 1:2) on silica gel to obtain N-(4-(diethylamino)benzyl)-N-pentylnaphthalene-1-sulfonamide (41). Yellow solid (308 mg, yield: 70%). $^1$H NMR (600 MHz, DMSO-d6) δ 8.47 (s, 1H), 8.19-8.17 (m, 1H), 8.14-8.12 (m, 1H), 8.07-8.05 (m, 1H), 7.84-7.82 (m, 1H), 7.73-7.69 (m, 2H), 7.07-7.05 (m, 2H), 6.58-6.56 (m, 2H), 4.22 (d, J=3.0 Hz, 2H), 3.30-3.27 (m, 4H), 3.06-3.03 (m, 2H), 1.33-1.23 (m, 2H), 1.05-1.04 (m, 4H), 1.02 (t, J=5.40 Hz, 6H), 0.65 (t, J=3.60 Hz, 3H). LC-MS (ESI): m/z 439.4 (M+H)+.

Example 40

N-(4-(diethylamino)benzyl)-N-pentyl-[1,1'-biphenyl]4-sulfonamide (42). The intermediate N,N-diethyl-4-((pentylamino)methyl)aniline (compound 35) (248 mg, 1.0 mmol) in dichloromethane (DCM, 10 mL) was chilled in an ice bath with the exclusion of moisture, and then triethylamine (TEA, 121 mg, 1.2 mmol) was added to it. The resulting solution was treated drop-wise under stirring with [1,1'-biphenyl]-4-sulfonyl chloride (252 mg, 1.0 mmol) in DCM over 30 minutes at 0° C. and then left overnight at room temperature. The reaction solution was poured into water and extracted with EA. The combined organic layers were washed with water and brine and then dried over $Na_2SO_4$. The mixture was filtered and the solvent was evaporated under vacuum. The residue was purified by flash chromatography (ethyl acetate/petroleum ether, 1:2) on silica gel to obtain N-(4-(diethylamino)benzyl)-N-pentyl-[1,1'-biphenyl]-4-sulfonamide (42). Yellow solid (272 mg, yield: 59%). $^1$H NMR (400 MHz, DMSO-d6) δ 7.90 (s, 4H), 7.77-7.75 (m, 2H), 7.56-7.52 (m, 2H), 7.48-7.44 (m, 1H), 7.08 (d, J=8.8 Hz, 2H), 6.61 (d, J=8.8 Hz, 2H), 4.20 (s, 2H), 3.32-3.28 (m, 4H), 3.04 (t, J=7.6, 2H), 1.30-1.27 (m, 2H), 1.6 (t, J=7.2, 6H), 0.71 (t, J=7.20 Hz, 3H). LC-MS (ESI): m/z 464.9 (M+H)+.

Radioligand Competition Binding Assays

The affinities of the synthesized ligands were determined in radioligand binding studies at human CB1 and CB2 receptors using [3H](—)-cis-3-[2-hydroxy-4-(1,1 dimethylheptyl)phenyl]-trans-4-(3-hydroxypropyl) cyclohexanol (CP55,940) as a CB receptor radioligand. As a source for human CB1 and CB2 receptors, membrane preparations of Chinese hamster ovary (CHO) cells stably expressing the respective receptor subtype were utilized (50 µg of protein/vial). CB2 selective ligand SR144528 (CB2 inverse agonist) and CB1 ligand SR141716 (CB1 inverse agonist) were used as positive controls, respectively, along with the tested compounds in bioassays experiments. Only compounds with high CB2 receptor binding potency was chosen to carry out the CB1 binding assay. CB ligand competition binding assay was carried out as described previously in Gertsch, J., et al., Beta-caryophyllene is a dietary cannabinoid. *Proc Natl Acad Sci USA* 2008, 105 (26), 9099-104. Briefly, non-radioactive (or cold) ligands (synthesized derivatives and reference ligands) were diluted in a binding buffer (50 mM Tris-HCl (pH 7.4), 5 mM MgC12, 2.5 mM EGTA, and 0.1% (w/v) fatty acid free BSA), supplemented with 10% dimethyl sulfoxide and 0.4% methyl cellulose. Each assay plate well contained a total of 200 µL of reaction mixture composed of 5 µg of CB1 (or 2.5 µg CB2) membrane protein, labeled [3H]-CP-55,940 ligand at a final concentration of 2.5 nM, and the unlabeled ligand at its varying dilutions as stated above. Plates were incubated at 30° C. for 1 hour with gentle shaking.

The reaction was terminated by rapid filtration through Unifilter GF/B filter plates using a Unifilter Cell Harvester (PerkinElmer). After the plate was allowed to dry overnight, 30 µL MicroScint-0 cocktail (PerkinElmer) was added to each well, and the radioactivity was counted using a PerkinElmer TopCounter. All assays were performed in duplicate and data points were represented as mean±S.E.M. Bound radioactivity data was analyzed for Ki values using non-linear regression analysis via GraphPad Prism 5.0 software.

The saturation binding of [3H]-CP-55,940 to the membrane proteins was performed as described previously. Briefly, the CB1 (or CB2) membrane fractions (5 µg) were incubated with 3 increasing concentrations of [3H]-CP-55,940 (0.05-4 nM) in 96-well plates at 30° C. with slow shaking for 1 hour. The incubation buffer was composed of 50 mM Tris-HCl (pH 7.4), 5 mM MgCl2, 2.5 mM EGTA, and 0.1% (w/v) fatty acid free BSA. The ligand was diluted in incubation buffer supplemented with 10% dimethyl sulfoxide and 0.4% methyl cellulose. Non-specific binding was determined in the presence of unlabeled CP-55,940 (5000 nM). The reaction was terminated and the radioactivity was counted as stated above. Non-linear regression analysis revealed the receptor density (Bmax) and the equilibrium dissociation constant (Kd) values of [3H]-CP-55,940 for the CB2 receptor.

Cyclic Adenosine Monophosphate (cAMP) Assay

Cyclic AMP levels were measured by performing the cell-based LANCE cAMP-384 kit assay (PerkinElmer) as previously described 13-14. The assay is based on the competition between the europium-labeled cAMP tracer complex and sample cAMP for binding sites on cAMP-specific antibodies. The antibodies are labeled with Alexa Fluor dye that is sensitive to energy emissions. Briefly, the cell-based LANCE cAMP assays were performed on 384-well ProxiPlates using CHO cells stably expressing the CB2 receptors at density of 2×10³ cells per well in 5 µL of RPMI-1640 medium (Gibco Laboratories, Grand Island, N.Y.) containing 1% dialyzed FBS, 25 mM HEPES, 100 µg/ml penicillin, 100 U/ml streptomycin, and 200 µg/ml of G-471. After incubation overnight, 2.5 µL of cAMP antibody and RO20-1724 (a phosphodiesterase inhibitor) in stimulation buffer (DPBS 1×, containing 0.1% BSA) was added to each well, followed by the addition of 2.5 µL of the compound plus the forskolin complex (an adenyl cyclase activator). After incubation at room temperature for 45 minutes, 10 µL of detection buffer was added into each well. The plate was then incubated at room temperature for 1 hour. The plate was then measured in a Synergy H1 hybrid reader (BioTek) with excitation at 340 nm and emission at 665 nm. The results represent at least two independent experiments each in triplicates. EC50 values were determined by non-linear regression dose-response curve (GraphPad Prism 5).

In-Vitro Osteoclast Formation Assay

Bone marrow (BM) cells were obtained from the tibia and femur of 4- to 6-week old C57BL/6 mice. To examine the effects of our selective CB2 ligands, BM cells were seeded at 2×10⁵ cells/well in 96-well plates in 100 µIL/well Alpha-MEM media (Gibco Laboratories, Grand Island, N.Y.) containing 15% fetal bovine serum (FBS) (Gibco Laboratories, Grand Island, N.Y.), 30 ng/mL M-CSF (R&D Systems, USA), and 100 ng/mL RANKL (ProsPec, East Brunswick, N.J.). Plates were cultured for 7-10 days. Half media was changed every third day with or without CB2 ligands. At the end of the experiment, cells were fixed and stained with tartrate-resistant acid phosphate (TRAP) (Sigma-Aldrich, USA), according to manufacturer's protocol. TRAP-positive cells with ≥3 nuclei were counted as osteoclasts ((a) Feng, R., et al., SDX-308, a nonsteroidal anti-inflammatory agent, inhibits NF-kappaB activity, resulting in strong inhibition of osteoclast formation/activity and multiple myeloma cell growth. *Blood* 2007, 109 (5), 2130-8; (b) Yu, M., et al., Curcumol suppresses RANKL-induced osteoclast formation by attenuating the JNK signaling pathway. *Biochem Biophys Res Commun* 2014, 447 (2), 364-70; (c) Feng, R., et al., KD5170, a novel mercaptoketone-based histone deacetylase inhibitor, exerts antimyeloma effects by DNA damage and mitochondrial signaling. *Mol Cancer Ther* 2008, 7 (6), 1494-505.).

MTT Cytotoxicity Assay

The cell-proliferation effect of our CB2 ligands on the osteoclast precursor RAW264.7 cells was assessed using MTT 3-(4,5-dimethylthiazol-2-yl)-2,5-diphenyltetrazolium bromide (Sigma, St. Louis, USA). Briefly, cells are seeded in a 96-well plate at a concentration of 1.5×10⁴ cells per well in RPMI-1640 medium (Gibco Laboratories, Grand Island, N.Y.) containing 5% FBS to a volume of 100 µL. Wells were divided into control and drug groups in triplicates. The control wells contained only the assay buffer with no drug. The synthesized CB2 ligands were added into the wells after dilution with DMSO and incubated for 48 hours at 37° C. and 5% $CO_2$. MTT solution (20 µL) was added to each well, shaken at 150 rpm for 5 minutes, and then incubated for 2-5 hours at 37° C. and 5% $CO_2$. The metabolism product (formazan) was dissolved in 200 µL DMSO and shaken at 150 rpm for 5 minutes. Optical density was read at 540 nm and subtracted from the background at 720 nm. The effect of ligands on cell viability was expressed as percent cell viability, with vehicle-treated control cells set at 100% (Feng, R., et al., KD5170, a novel mercaptoketone-based histone deacetylase inhibitor, exerts antimyeloma effects by DNA damage and mitochondrial signaling. *Mol Cancer Ther* 2008, 7 (6), 1494-505).

SAR Strategies

We first aimed at replacing the p-nitrophenyl group in the lead compound with p-(diethylamino)benzyl group, as previous studies have shown that this fragment contributed to the selectivity towards the CB2 receptor 13, replacing one of the sulfonyl groups with 3,4,5-trimethoxybenzylamine, 3-(aminomethyl)pyridine, piperonylamine, and pentanamine, as well as retaining and/or removing the other sulfonyl. Our studies have shown that the removal of one of the hydrophobic groups dramatically decreased the CB2 binding affinity (compounds 3, 20, 28, and 36; CB2 Ki=42, 350 nM>20,000 nM>20,000 nM and 40,170 nM, respectively, Tables 1-4), indicating the necessity of introducing hydrophobic groups at the R1 and R2 positions to retain binding activities.

TABLE 1
Chemical structures, physicochemical properties, radioligand competition binding affinity, and selectivity index for series 1 derivatives (Compounds 3-18):
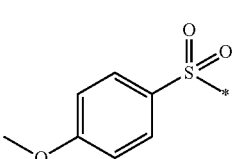
| Entry | R | MW | cLogP | $K_i$ (CB2), nM | $K_i$ (CB1), nM | SI |
|---|---|---|---|---|---|---|
| 3 | H | 358.5 | 3.19 | 42350 | NT | — |
| 4 | 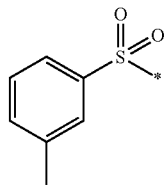 | 528.7 | 5.47 | 410 | NB | 50 |
| 5 | 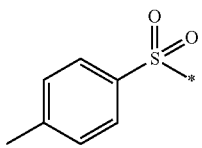 | 512.7 | 5.80 | 291 | 732 | 3 |
| 6 | 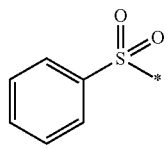 | 512.7 | 5.80 | 387 | 774 | 2 |
| 7 | 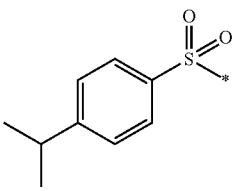 | 498.6 | 5.30 | 453 | NB | 44 |
| 8 | 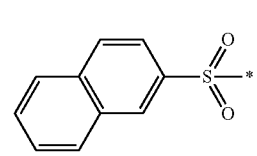 | 540.7 | 6.72 | 230 | 122 | — |
| 9 |  | 548.7 | 6.47 | 239 | 71 | — |

TABLE 1-continued
Chemical structures, physicochemical properties, radioligand competition binding affinity, and selectivity index for series 1 derivatives (Compounds 3-18):
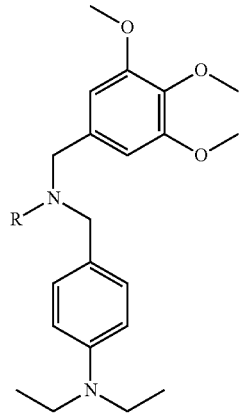
| Entry | R | MW | cLogP | $K_i$ (CB2), nM | $K_i$ (CB1), nM | SI |
|---|---|---|---|---|---|---|
| 10 | 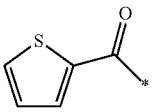 | 574.7 | 7.18 | 322 | NB | 62 |
| 11 | 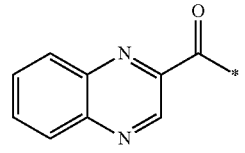 | 468.6 | 4.86 | 107 | 3282 | 31 |
| 12 | 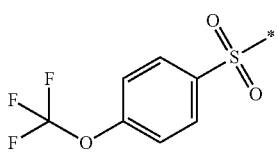 | 514.6 | 4.62 | 249 | 13020 | 52 |
| 13 | 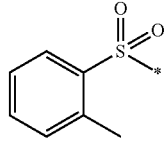 | 582.6 | 6.57 | 990 | 1240 | 2 |
| 14 | 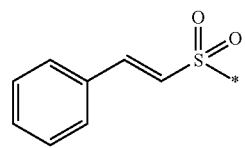 | 512.7 | 5.80 | 157 | 180 | 2 |
| 15 | 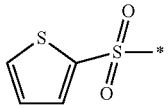 | 524.7 | 5.94 | 138 | NB | 145 |
| 16 |  | 504.7 | 5.02 | 639 | NB | 32 |

TABLE 1-continued

Chemical structures, physicochemical properties, radioligand competition binding affinity, and selectivity index for series 1 derivatives (Compounds 3-18):

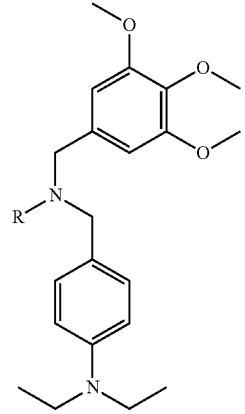

| Entry | R | MW | cLogP | $K_i$ (CB2), nM | $K_i$ (CB1), nM | SI |
|---|---|---|---|---|---|---|
| 17 | | 558.7 | 5.17 | 657 | NT | — |
| 18 | | 526.7 | 4.87 | 242 | 2290 | 9 |

Binding affinities for CB1 and CB2 receptor were evaluated using [3H]CP-55,940 radioligand competition binding assay. NB: no binding, Ki>20000 nM. NT: not tested. SI: selectivity index for CB2, calculated as Ki(CB1)/Ki(CB2) ratio. CB2 reference compound SR144528. CB1 reference compound SR141716.

Without wishing to be bound by theory, Applicants introduced (3,4,5-trimethoxyphenyl)methanamine fragment at the R1 position and synthesized 16 compounds (3-18, Table 1). These compounds differ in the R2 position by replacing the phenylmethanesulfonyl fragment with different functional groups, size, and properties. Compared with compound 1, reducing the distance between the benzene ring and the sulfonyl group by removing the methyl group and replacing the other phenylmethanesulfonyl with (3,4,5-trimethoxyphenyl)methanamine fragment increased the CB2 binding activity (compound 7, CB2 Ki=453 nM) with no affinity towards the CB1 receptor. This indicates that the distance between the benzene ring and the sulfonyl group should be narrow, and the other phenylmethanesulfonyl at the R2 position is not necessary for selectivity, which can be replaced with other fragments. To test the substitutions on the benzene ring of the benzene sulfonyl group, we introduced different substituents at different positions on the ring. The introduction of p-methyl group retained the CB2 binding affinity but induced the CB1 binding affinity (compound 6, CB2 Ki=387 nM, CB1 Ki=774 nM, selectivity index=2). Further, the introduction of m-methyl group improved the CB2 binding affinity yet retained good CB1 binding affinity (compound 5, CB2 Ki=291 nM, CB1 Ki=732 nM, selectivity index=2.5). In addition, ortho-substitutions on the benzene ring increased the CB2 binding affinity as well as increasing the CB1 binding affinity (compound 14, CB2 Ki=157 nM, CB1 Ki=180 nM, selectivity index=2). These results indicate that para substituents may be preferred over meta- and ortho- substitutions in increasing CB2 binding affinity and selectivity.

Different functional groups were tested at the para position. The introduction of a methoxy group at the para position retained good CB2 binding affinity with no CB1 binding affinity (compound 4, CB2 Ki=410 nM). However, introducing the p-isopropyl group improved the CB2 binding affinity, but the CB1 binding affinity is much higher (compound 8, CB2 Ki=230 nM, CB1 Ki=122 nM). Introducing trifluoromethoxy at the para position reduced the CB2 binding affinity and selectivity (compound 13, CB2 Ki=990 nM, CB1 Ki=1240 nM, selectivity index=2). Introduction of a p-formyl group improved CB2 binding affinity and selectivity (compound 18, CB2 Ki=242 nM, CB1 Ki=2290, selectivity index=9).

Different group sizes at the R2 position were also explored. The introduction of naphthalene-2-sulfonyl at the R2 position increased the CB1 binding affinity (compound 9, CB2 Ki=239 nM, CB1 Ki=71 nM). Further, the introduction of [1,1'-biphenyl]-4-sulfonyl at the R2 position abolished the CB1 binding affinity and improved the CB2 binding affinity (compound 10, CB2 Ki=322 nM, CB1 Ki>20000 nM).

The effect of introducing heterocycle groups at the R2 position was also explored. The introduction of a small heterocyclic group at the R2 position (thiophene-2-sulfonyl)

showed an increase in the CB2 binding affinity without affecting CB1 binding affinity (compound 16, CB2 Ki=639 nM, CB1 Ki>20000 nM). However, the introduction of a heterocyclic group with the replacement of the sulfonyl group with carbonyl group dramatically increased the CB2 binding affinity (compound 11, CB2 Ki=107 nM, CB1 Ki=3282 nM, selectivity index=31).

In addition, large heterocyclic groups at the R2 position were explored by introducing quinoxaline-2-carbonyl. The CB2 binding affinity and selectivity was greatly improved (compound 12, CB2 Ki=249 nM, CB1 Ki=13020 nM, selectivity index=52). These results indicated that introducing heterocyclic rings at the R2 position would potentiate the affinity and selectivity towards the CB2 receptor. Finally, to increase the conjugation system between the two functional groups (sulfonyl and the benzyl ring) of the fragment at the R2 position, a double bond between the two functional groups was introduced. This modification improved dramatically the CB2 binding affinity and selectivity (compound 15, CB2 Ki=138 nM, CB1 Ki>20000 nM).

TABLE 2

Chemical structures, physicochemical properties, radioligand competition binding affinity, and selectivity index for series 2 derivatives (Compounds 20-26):

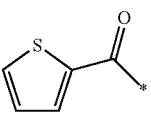

| Entry | R | MW | cLogP | $K_i$ (CB2), nM | $K_i$ (CB1), nM | SI |
|---|---|---|---|---|---|---|
| 20 | H | 269.4 | 2.39 | NB | NT | — |
| 21 | 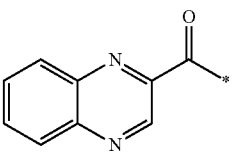 | 379.5 | 4.07 | 1020 | NT | — |
| 22 | 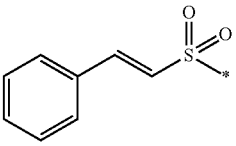 | 425.5 | 3.83 | 1205 | NT | — |
| 23 | 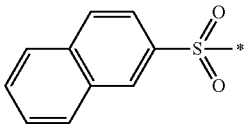 | 435.6 | 5.14 | 899 | 5460 | 6 |
| 24 | 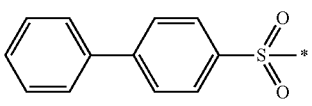 | 459.6 | 5.67 | 866 | 12040 | 14 |
| 25 | | 485.7 | 6.39 | 946 | NB | 21 |

Binding affinities for CB1 and CB2 receptor were evaluated using [3H]CP-55,940 radioligand competition binding assay. NB: no binding, Ki>20000 nM. NT: not tested. SI: selectivity index for CB2, calculated as Ki(CB1)/Ki(CB2) ratio. CB2 reference compound SR144528. CB1 reference compound SR141716.

Without wishing to be bound by theory, the 4-(diethylamino)benzyl group was retained and one of the phenylmethanesulfonyl was replaced with a heterocyclic group, 3-(aminomethyl)pyridine, and the other phenylmethanesulfonyl was replaced with different sulfonyl and carbonyl groups to evaluate the effect on reducing the size of the fragment at the R1 on the binding affinity and selectivity (compounds 20-26, Table 2). Introducing a bulky non-heterocyclic group at the R2 position improved the CB2 binding affinity (compounds 24 and 25, CB2 Ki<1000 nM). In addition, introducing a double bond between the sulfonyl and the benzyl group improved the CB2 binding affinity and selectivity (compound 23, CB2 Ki=899 nM, CB1 Ki=5460 nM, selectivity index=6).

TABLE 3

Chemical structures, physicochemical properties, radioligand competition binding affinity, and selectivity index for series derivatives (Compounds 28-34):

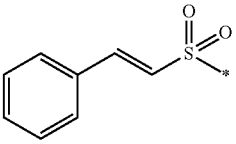

| Entry | R | MW | cLogP | $K_i$ (CB2), nM | $K_i$ (CB1), nM | SI |
|---|---|---|---|---|---|---|
| 28 | H | 312.4 | 3.86 | NB | NT | NT |
| 29 | 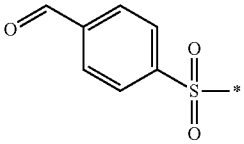 | 478.6 | 6.60 | 381 | 1159 | 3 |
| 30 | 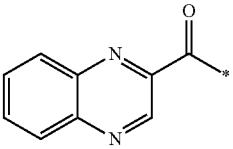 | 480.6 | 5.53 | 1872 | 2745 | 1 |
| 31 | 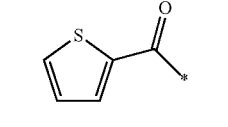 | 454.6 | 5.74 | 775 | 1267 | 2 |
| 32 | 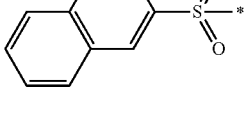 | 422.5 | 5.53 | 574 | 727 | 2 |
| 33 | 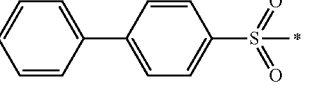 | 502.6 | 7.14 | 882 | NT | — |
| 34 | | 528.7 | 7.85 | 1995 | NT | — |

Binding affinities for CB1 and CB2 receptor were evaluated using [3H]CP-55,940 radioligand competition binding assay. NB: no binding, Ki>20000 nM. NT: not tested. SI: selectivity index for CB2, calculated as Ki(CB1)/Ki(CB2) ratio. CB2 reference compound SR144528. CB1 reference compound SR141716.

Without wishing to be bound by theory, one of the phenylmethanesulfonyl was replaced with the fragment piperonylamine and the other phenylmethanesulfonyl with different sulfonyl and carbonyl groups (compounds 28-34, Table 3). Replacing the phenylmethanesulfonyl at the R2 position with a bulky heterocyclic group showed good CB2 binding affinity with weak CB1 binding affinity (compound 31, CB2 Ki=775 nM, CB1 Ki=1267 nM, selectivity index=2). In contrast, smaller heterocyclic groups tried abolished the CB2 selectivity (compound 32, CB2 Ki=574 nM, CB1 Ki=727 nM), indicating that the presence of two bulky heterocyclic groups at positions R1 and R2 improved the CB2 affinity and selectivity. This result is further confirmed by replacing phenylmethanesulfonyl at the R2 position with 4-formylbenzenesulfonyl which showed a reduction in CB2 affinity and selectivity (compound 30, CB2 Ki=1872 nM, CB1 Ki=2745 nM, selectivity index=1). Similarly, the introduction of a double bond between the sulfonyl and the benzyl group showed good CB2 binding affinity as well as selectivity (compound 29, CB2 Ki=381 nM, CB1 Ki=1159 nM, selectivity index=3).

TABLE 4

Chemical structure, physicochemical properties, radioligand competition binding affinity, and selectivity index for series 4 derivatives (Compounds 36-42):

| Entry | R | MW | cLogP | $K_i$ (CB2), nM | $K_i$ (CB1), nM | SI |
|---|---|---|---|---|---|---|
| 36 | H | 248.4 | 4.85 | 40170 | NT | NT |
| 37 | (E)-styrylsulfonyl | 414.6 | 6.61 | 515 | 5242 | 10 |
| 38 | 4-formylbenzenesulfonyl | 416.6 | 6.02 | 657 | 1786 | 3 |
| 39 | quinoxaline-2-carbonyl | 404.6 | 5.67 | 1852 | 1863 | 1 |
| 40 | thiophene-2-carbonyl | 358.5 | 5.91 | 362 | 2437 | 7 |
| 41 | naphthalene-2-sulfonyl | 438.6 | 7.62 | 1139 | NT | — |
| 42 | biphenyl-4-sulfonyl | 464.7 | 8.33 | 3147 | NT | — |

Binding affinities for CB1 and CB2 receptor were evaluated using [3H]CP-55,940 radioligand competition binding assay. NB: no binding, Ki>20000 nM. NT: not tested. SI: selectivity index for CB2, calculated as Ki(CB1)/Ki(CB2) ratio. CB2 reference compound SR144528. CB1 reference compound SR141716.

Without wishing to be bound by theory, one of the phenylmethanesulfonyl was replaced with pentanamine to examine the effect of replacing aromatic groups with aliphatic groups (compounds 36-42, Table 4). Introducing a double bond between the sulfonyl and the benzyl group exhibited an increase in the CB2 affinity and selectivity (compound 37, CB2 Ki=515 nM, CB1 Ki=5242 nM, selectivity index=10). In addition, small heterocyclic groups showed good CB2 affinity and selectivity (compound 40, CB2 Ki=362 nM, CB1 Ki=2437 nM, selectivity index=7). However, in some instances, bulky heterocyclic groups abolished CB2 selectivity (compound 39, CB2 Ki=1852 nM, CB1 Ki=1863 nM). These results showed that it is not necessary to retain aromatic properties at all positions, and the introduction of an aliphatic group will retain the CB2 binding affinity and selectivity but to a lesser extent than aromatic groups.

In-Vitro Functional Activity of the CB2 Ligands

Figure 4:
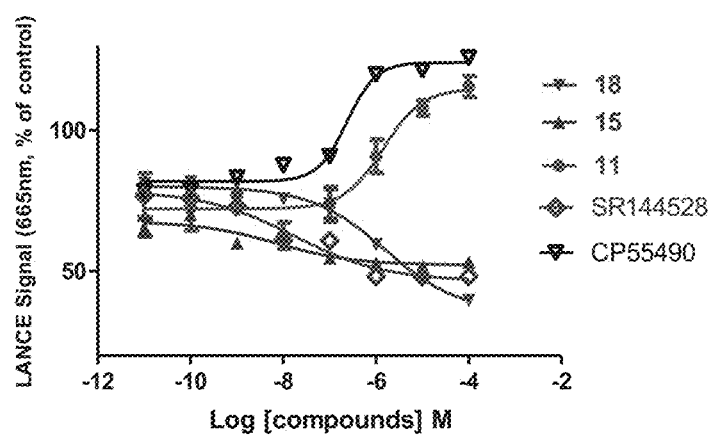
FIG. 4 relates to cAMP Assay Results. LANCE signal of CB2 ligands. Stably transfected CHO cells expressing human CB2 receptors were utilized to carry out the LANCE cAMP assay. The LANCE signal exhibited different concentration-dependent results with different CB2 ligands. Data is mean±SEM of all experiments of two or more performed in triplicate.

CB2 functional activities of our synthesized compounds were investigated by using the cell-based LANCE cAMP assay, which can be used to distinguish between agonists, inverse agonists, and neutral antagonists. The LANCE cAMP assay was carried out to measure the functional activities of our synthesized CB2 selective ligands as previously described 14. Briefly, the assay was performed on 384-well plates using CHO cells stably expressing CB2 receptors in the presence of phosphodiesterase inhibitor, RO-20-1724 and adenyl cyclase activator, forskolin. As shown in FIG. 4, reduction of the LANCE signal occurred with increasing concentrations of compounds 15, 18, and SR-144,528. These ligands act as inverse agonists, indicated by increasing forskolin-induced cAMP production. On the other hand, compound 11 and the agonist, CP55940, inhibit cAMP production, which indicates that compound 11 is a CB2 selective agonist.

Osteoclast Formation Assay

Cannabinoids have been known to modulate and maintain bone remodeling and balance (Ofek et al., Peripheral cannabinoid receptor, CB2, regulates bone mass. *Proc Natl Acad Sci USA* 2006, 103 (3), 696-701, (a) Bab et al., Cannabinoid receptors and the regulation of bone mass. *Br J Pharmacol* 2008, 153 (2), 182-8; (b) Bab et al., Cannabinoids and the skeleton: from marijuana to reversal of bone loss. *Ann Med* 2009, 41 (8), 560-7; (c) Idris et al., Regulation of bone mass, osteoclast function, and ovariectomy-induced bone loss by the type 2 cannabinoid receptor. *Endocrinology* 2008, 149 (11), 5619-26.). CB2 receptors have been shown to be involved in osteoporosis, suggesting the CB2 receptors as promising targets for osteoporosis. Three compounds (15, 18, and 11) were selected to evaluate their activity against the receptor-activator of nuclear factor kappa-B ligand (RANKL)-induced osteoclast differentiation on 4- to 6-week old C57BL/6 mouse bone marrow cells. As shown in FIG. 5, compounds 15 and 18 induced a concentration-dependent inhibition of osteoclast formation showing a strong inhibition at 10 μM (inhibition rates>95%). These results are consistent with their CB2 binding affinity. However, compound 11 showed an induction of osteoclast formation at higher doses (10 μM). This data suggests that CB2 inverse agonists are more promising than CB2 agonists for the inhibition of osteoclast formation and ultimately for osteoporosis treatment. Our results are also consistent with several previous reports (Yang, P. et al., Lead Discovery, Chemistry Optimization, and Biological Evaluation Studies of Novel Biamide Derivatives as CB(2) Receptor Inverse Agonists and Osteoclast Inhibitors. J Med Chem 2012.).

Cytotoxicity Studies of Compounds 15 and 18

The cytotoxicity assay was carried out to exclude that the high osteoclast formation inhibition effects were not due to the toxicity of the newly discovered compounds. The cytotoxic effects were measured by utilizing the MTT cell-viability assay. Osteoclast precursor cell-line, RAW 264.7 cells, were seeded on a 96-well plate and incubated with compounds 15 and 18 for 48 hours. An MTT assay kit was utilized to determine the percentage of cell survival (van Meerloo, J, et al., Cell sensitivity assays: the MTT assay. *Methods Mol Biol* 2011, 731, 237-45.). As shown in FIG. 5, cell viability was not significantly altered by the tested compound as compared to the control group. Both compounds had minimal effects at doses of 2.5, 5.0, and 10 μM with low effects at higher doses (20 μM). These results showed that the good anti-osteoclast activity of our newly discovered compounds was not due to their cytotoxicity, which means favorable therapeutic indices of our new CB2 ligands.

The above examples are given to illustrate the present invention. It should be understood, however, that the spirit and scope of the invention is not to be limited to the specific conditions or details described in these examples. All publicly available documents referenced herein, including but not limited to U.S. patents, are specifically incorporated by reference.

What is claimed is:
1. A method for treating multiple myeloma in a mammal in need thereof by modulating the activity of a cannabinoid receptor-2 (CB2), comprising administering to the mammal a therapeutically effective amount of a compound represented by Formula (I):

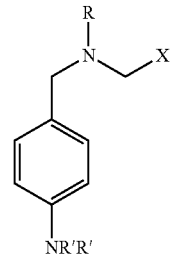

wherein:
R is A-B-Y;
A is —SO$_2$— or —C(O)—;
B is a bond or —CHCH—;
X is selected from the group consisting of substituted phenyl, substituted or unsubstituted pyridine, and substituted or unsubstituted C$_{3-5}$ alkyl, wherein the substituted phenyl, pyridine and alkyl is substituted with two or three moieties selected from C$_{1-4}$ alkyl, C$_{1-4}$ alkoxy, —C(O)H, C$_{1-4}$ perfluroalkyl, and C$_{1-4}$ perfluroalkoxy, or the substituted phenyl or pyridine is substituted with —O—(CH$_2$)$_{1-2}$—O— where the O molecules are covalently bound to adjacent carbon atoms on the substituted phenyl or pyridine;
Y is a ringed moiety selected from phenyl, naphthyl, and thiophenyl, wherein one or two of the ring carbons is optionally replaced with N, and wherein the ringed moiety is optionally substituted with one to three C$_{1-4}$ alkyl, C$_{1-4}$ alkoxy, —C(O)H, C$_{1-4}$ perfluroalkyl, C$_{1-4}$ perfluroalkoxy, or substituted or unsubstituted phenyl; and
R' is, in each instance a C$_{1-6}$ alkyl,
or a pharmaceutically acceptable salt thereof.

2. A method for treating osteoporosis in a mammal in need thereof by modulating the activity of a cannabinoid receptor-2 (CB2), comprising administering to the mammal a therapeutically effective amount of a compound represented by Formula (I):

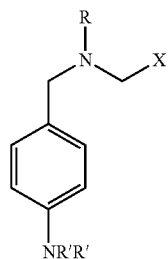

wherein:
R is A-B-Y;
A is —SO$_2$— or —C(O)—;
B is a bond or —CHCH—;
X is selected from the group consisting of substituted phenyl, substituted or unsubstituted pyridine, and substituted or unsubstituted C$_{3-5}$ alkyl, wherein the substituted phenyl, pyridine and alkyl is substituted with two or three moieties selected from C$_{1-4}$ alkyl, C$_{1-4}$ alkoxy, —C(O)H, C$_{1-4}$ perfluroalkyl, and C$_{1-4}$ perfluroalkoxy, or the substituted phenyl or pyridine is substituted with —O—(CH$_2$)$_{1-2}$—O— where the 0 molecules are covalently bound to adjacent carbon atoms on the substituted phenyl or pyridine;
Y is a ringed moiety selected from phenyl, naphthyl, and thiophenyl, wherein one or two of the ring carbons is optionally replaced with N, and wherein the ringed moiety is optionally substituted with one to three C$_{1-4}$ alkyl, C$_{1-4}$ alkoxy, —C(O)H, C$_{1-4}$ perfluroalkyl, C$_{1-4}$ perfluroalkoxy, or substituted or unsubstituted phenyl; and
R' is, in each instance a C$_{1-6}$ alkyl,
or a pharmaceutically acceptable salt thereof.

3. A method for modulating the activity of a cannabinoid receptor-2 (CB2) in a mammal in need thereof, comprising contacting the CB-2 receptor with a compound represented by Formula (I):

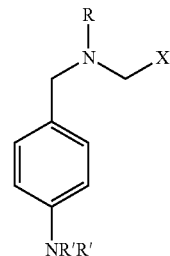

wherein:
R is A-B-Y;
A is —SO$_2$— or —C(O)—;
B is a bond or —CHCH—;
X is selected from the group consisting of substituted phenyl, substituted or unsubstituted pyridine, and substituted or unsubstituted C$_{3-5}$ alkyl, wherein the substituted phenyl, pyridine and alkyl is substituted with two or three moieties selected from C$_{1-4}$ alkyl, C$_{1-4}$ alkoxy, —C(O)H, C$_{1-4}$ perfluroalkyl, and C$_{1-4}$ perfluroalkoxy, or the substituted phenyl or pyridine is substituted with —O—(CH$_2$)$_{1-2}$—O— where the O molecules are covalently bound to adjacent carbon atoms on the substituted phenyl or pyridine;
Y is a ringed moiety selected from phenyl, naphthyl, and thiophenyl, wherein one or two of the ring carbons is optionally replaced with N, and wherein the ringed moiety is optionally substituted with one to three C$_{1-4}$ alkyl, C$_{1-4}$ alkoxy, —C(O)H, C$_{1-4}$ perfluroalkyl, C$_{1-4}$ perfluroalkoxy, or substituted or unsubstituted phenyl; and
R' is, in each instance a C$_{1-6}$ alkyl,
or a pharmaceutically acceptable salt thereof.

4. The method of claim 1, wherein:
(a) A is SO$_2$; and/or
(b) B is a bond; and/or
(c) B is —CHCH—; and/or
(d) X is phenyl substituted with three C$_{1-4}$ alkoxy; and/or
(e) X is phenyl substituted with three methoxy; and/or
(f) X is phenyl substituted with —O—(CH$_2$)$_{1-2}$—O—; and/or
(g) X is unsubstituted pyridine; and/or
(h) X is an unsubstituted C$_{3-5}$ alkyl; and/or
(i) X is selected from

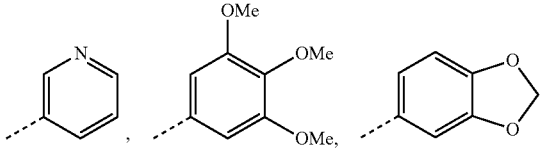

and n-pentyl; and/or
(j) Y is phenyl; and/or
(k) Y is phenyl, and is substituted only at the para position; and/or
(l) R is selected from the R groups in Tables 1-4; and/or
(m) Y is selected from the Y groups in Tables 1-4.

5. The method of claim 1, wherein the compound is co-administered with a drug useful in treating multiple myeloma.

6. The method of claim 5, wherein the drug comprises one or more of lenalidomide, dexamethasone, and bortezomib.

7. The method of claim 5, wherein the compound of Formula (I) is co-administered before administration of the drug useful in treating multiple myeloma.

8. The method of claim 5, wherein the compound of Formula (I) is co-administered during administration of the drug useful in treating multiple myeloma.

9. The method of claim 5, wherein the compound of Formula (I) is co-administered after administration of the drug useful in treating multiple myeloma.

10. The method of claim 2, wherein:
(a) A is $SO_2$; and/or
(b) B is a bond; and/or
(c) B is —CHCH—; and/or
(d) X is phenyl substituted with three $C_{1-4}$ alkoxy; and/or
(e) X is phenyl substituted with three methoxy; and/or
(f) X is phenyl substituted with —O—$(CH_2)_{1-2}$—O—; and/or
(g) X is unsubstituted pyridine; and/or
(h) X is an unsubstituted $C_{3-5}$ alkyl; and/or
(i) X is selected from

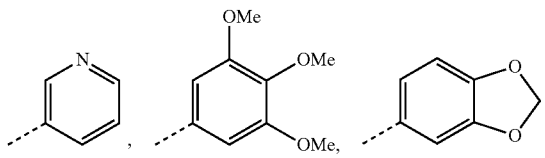

and n-pentyl; and/or
(j) Y is phenyl; and/or
(k) Y is phenyl, and is substituted only at the para position; and/or
(l) R is selected from the R groups in Tables 1-4; and/or
(m) Y is selected from the Y groups in Tables 1-4.

11. The method of claim 2, wherein the compound is co-administered with a drug useful in treating osteoporosis.

12. The method of claim 11, wherein the drug comprises one or more of estrogen therapy, a selective estrogen receptor modulator, a bisphosphonate, and calcitonin.

13. The method of claim 11, wherein the compound of Formula (I) is co-administered before administration of the drug useful in treating osteoporosis.

14. The method of claim 11, wherein the compound of Formula (I) is co-administered during administration of the drug useful in treating osteoporosis.

15. The method of claim 11, wherein the compound of Formula (I) is co-administered after administration of the drug useful in treating osteoporosis.

16. The method of claim 2, wherein the mammal is a post-menopausal female who suffers from bone loss or post-menopausal osteoporosis.

17. The method of claim 2, wherein the mammal is a cancer patient who received chemotherapy or radiation therapy.

18. The method of claim 17, wherein the radiation therapy comprises pelvic radiotherapy.

19. The method of claim 2, wherein the mammal is at increased risk of bone loss or osteoporosis due to aging, menopause, other medications, therapies, or any combination thereof.

20. The method of claim 2, wherein the method comprises: (i) performing a bone scan or any other means to measure bone density to assess the bone density of the mammal to determine whether the mammal suffers from osteopenia, osteoporosis, or bone loss, or whether the mammal has declining bone density suspected to lead to osteopenia, osteoporosis or bone loss; and (ii) administering the therapeutically effective amount of a compound represented by Formula (I).

21. The method of claim 3, wherein:
(a) A is $SO_2$; and/or
(b) B is a bond; and/or
(c) B is —CHCH—; and/or
(d) X is phenyl substituted with three $C_{1-4}$ alkoxy; and/or
(e) X is phenyl substituted with three methoxy; and/or
(f) X is phenyl substituted with —O—$(CH_2)_{1-2}$—O—; and/or
(g) X is unsubstituted pyridine; and/or
(h) X is an unsubstituted $C_{3-5}$ alkyl; and/or
(i) X is selected from

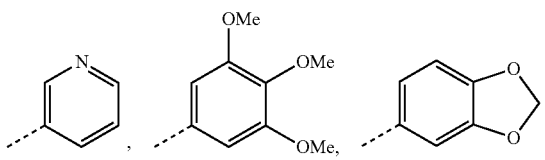

and n-pentyl; and/or
(j) Y is phenyl; and/or
(k) Y is phenyl, and is substituted only at the para position; and/or
(l) R is selected from the R groups in Tables 1-4; and/or
(m) Y is selected from the Y groups in Tables 1-4.

* * * * *